United States Patent [19]

Albright et al.

[11] Patent Number: 5,106,835

[45] Date of Patent: Apr. 21, 1992

[54] RENIN INHIBITORS

[75] Inventors: Jay D. Albright, Nanuet; Fuk-Wah Sum, New City, both of N.Y.; Charles F. Howell, Upper Saddle River, N.J.

[73] Assignee: American Cyanamid Company, Stamford, Conn.

[21] Appl. No.: 543,620

[22] Filed: Jun. 22, 1990

Related U.S. Application Data

[63] Continuation-in-part of Ser. No. 290,079, Dec. 27, 1988, abandoned.

[51] Int. Cl.$^5$ .............................................. A61K 37/00
[52] U.S. Cl. .......................................... 514/18; 514/19
[58] Field of Search ..................................... 514/18, 19

[56] References Cited

U.S. PATENT DOCUMENTS 4,863,904 9/1989 Iizuka et al. ............................ 514/18
4,981,843 1/1991 Ryono et al. ........................... 514/18

FOREIGN PATENT DOCUMENTS 0186977 5/1986 European Pat. Off. ............ 530/331

OTHER PUBLICATIONS

Burger, *Medicinal Chemistry*, 1960, pp. 565-571, 578-581, 600-601.
Denkewatter et al. *Progress In Drug Research*, 1966, vol. 10, pp. 610-612.
Plattner et al. *J. Med. Chem.* 1988, 31 (12):2277-2288.
Bolis et al. *J. Med. Chem.* 1987, 30 (10):1729-1737.
Haber et al. *J. Cardiovasc. Pharmacol.* 1987, 10 (Suppl. 7):554-558.

*Primary Examiner*—Lester L. Lee
*Assistant Examiner*—E. J. Kraus
*Attorney, Agent, or Firm*—H. G. Jackson

[57] ABSTRACT

The invention is new renin inhibitor dipeptide and tripeptide derivatives of the formula:

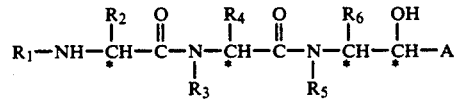

30 Claims, No Drawings

RENIN INHIBITORS

SUMMARY OF THE INVENTION

This application is a continuation-in-part of pending application Ser. No. 07/290,079 filed Dec. 27, 1988 and now abandoned.

This invention relates to new dipeptide and tripeptide derivatives of formula I

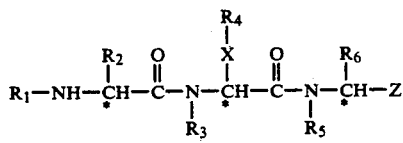

Formula I wherein $R_1$ is hydrogen,

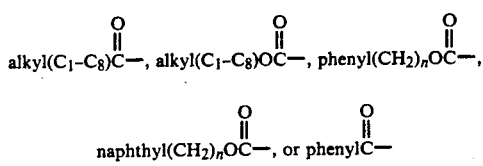

where n is an integer 1–4 or the moieties: $R_1$-L-prolyl, $R_1$-L-thiopropyl, $R_1$-L-seryl, $R_1$-L-methionyl, $R_1$-L-alanyl, $R_1$-L-phenylalanyl, $R_1$-L-(S-benzyl)cysteinyl, $R_1$-L-histidyl or $R_1$-glycyl; $R_2$ is phenylmethyl, (2-thienyl)CH$_2$, (3-indolyl)CH$_2$—, or —CH$_2$-naphthyl; $R_3$ is hydrogen or methyl; $R_4$ is alkyl(C$_1$–C$_8$), —(CH$_2$)$_n$NH$_2$, (4-imidazolyl)CH$_2$—, phenylmethyl, phenyl, cyclohexyl, CH$_2$CH$_2$N[alkyl(C$_1$–C$_3$)]$_2$ or (CH$_2$)$_n$-X-alkyl(C$_1$–C$_3$), $R_5$ is hydrogen, or methyl; $R_6$ is alkyl(C$_1$–C$_6$), phenylmethyl, cyclohexylmethyl, —(CH$_2$)n-X-alkyl(C$_1$–C$_3$) or

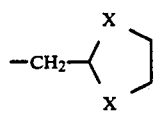

X is —O— or —S—; Z is —CHO or —CH(OH)A where A is

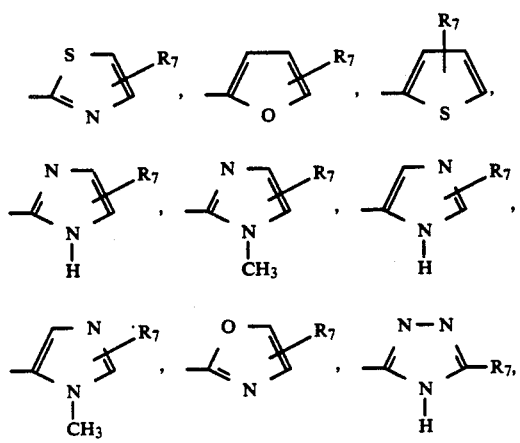

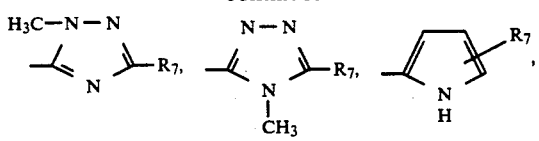

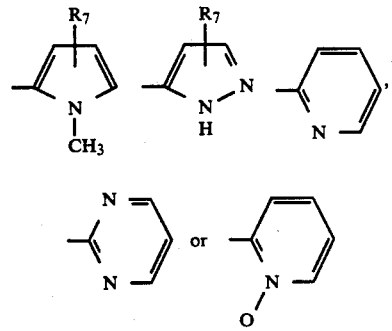

with provisio that when A is

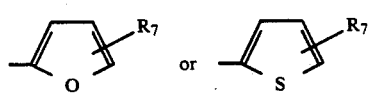

then X in formula I may also be a single bond; $R_7$ is hydrogen, alkyl(C$_1$–C$_3$) or COR$_8$, and $R_8$ is NH$_2$, OH, —O—alkyl(C$_1$–C$_4$), —NH-alkyl(C$_1$–C$_4$), —N[alkyl(-C$_1$—C$_3$)]$_2$ or

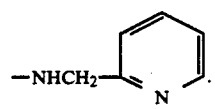

In formula I the asterisks denote asymmetric carbon atoms.

DETAILED DESCRIPTION OF THE INVENTION

Within the group of compounds defined by formula I, certain subgroups of compounds are preferred. Broadly preferred are those compounds where the α-amino acids have the natural L configuration. Thus the most preferred are those compounds where the dipeptide or the tripeptide unit in formula I has the L, L or the L, L, L configuration. Especially preferred in the C-terminal units are compounds were the C-terminal units are selected from those of formula II

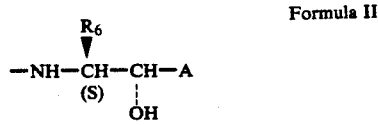

Formula II with an anti(threo) relationship between the amino group and the hydroxyl group. Most preferred of the 1-amino-2-hydroxy compounds of formula II are those diastereomers with the 1S configuration.

Most preferred of the compounds of formula I, wherein the C terminal group is represented by formula II, are those compounds wherein $R_1$ is

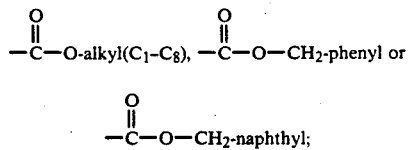

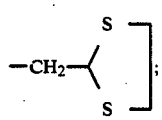

$R_2$ is phenylmethyl (3-indolyl)$CH_2$—, (2-thienyl)$CH_2$— or $CH_2$—naphthyl; $R_3$ is hydrogen; $R_4$ is alkyl($C_1$-$C_8$), (4-imidazolyl)$CH_2$— or $CH_2CH_2N[alkyl(C_1$-$C_3)]_2$; $R_5$ is hydrogen; $R_6$ is alkyl($C_1$-$C_8$), cyclohexylmethyl or

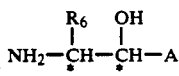

Z is —CH(OH)-A where A and $R_7$ and X are as previously defined; and $R_8$ is $NH_2$, OH, —O-alkyl($C_1$-$C_4$) or NH alkyl($C_1$-$C_4$).

The products of formula I and the preferred subgroups can be prepared by various synthetic procedures.

For example, the products can be prepared by reacting an N-protected depeptide of formula III:

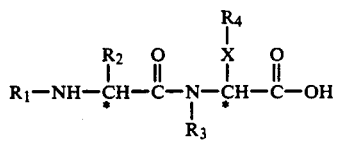
Formula III or its chemical equivalent with a 1-amino-2-hydroxy compound of formula IV, $$\underset{NH_2-\overset{*}{C}H-\overset{*}{C}H-A}{\overset{R_6\quad OH}{|\quad\;\;|}} \quad \text{Formula IV}$$

Thus a dipeptide of formula III is reacted with a peptide coupling reagent to convert the carboxyl group into an activated derivative which is then reacted with a compound of formula IV, or its chemical equivalent to give the products of this invention.

Preferred peptide coupling reagents are those which do not cause racemization at the carbons designated with asterisks. For example, appropriate peptide coupling reagents are:
1) N,N'-Dicyclohexylcarbodiimide plus 1-hydroxybenzotriazole
2) Benzotriazol-1-yloxytris (dimethylamino)phosphonium hexafluorophosphate (BOP-reagent)
3) N,N'-Bis[2-oxo-3-oxazolidinyl]phosphorodiamidic chloride (BOB-Cl)
4) Diphenylphosphinyl chloride (DPP-Cl)
5) Diethoxyphosphoryl cyanide
6) 2-Chloro-1-methylpyridinium iodide
7) Phenyldichlorophosphate plus imidazole In the compounds of formula III, where $R_4$ is 4-imidazolylmethyl, the imidazole nitrogen is blocked with an appropriate group such as tosyl, 2,4-dinitrophenyl, benzyl, or benyloxymethyl, prior to coupling with compounds of formula IV. A suitable blocking group is chosen so that conditions for its removal are compatible with other structural features in the product of formula I.

Alternatively a peptide of formula III is activated with an appropriate peptide coupling reagent and then reacted with a compound of formula V in which the hydroxy group is protected with a removable blocking group Y. Suitable blocking groups are represented by trimethylsilyl t-butyldimethylsilyl, tetrahydropyranyl, acetyl, benzoyl and the like. Removal of the hydroxyl blocking group then gives the compounds of formula I where Z is —CH(OH)A

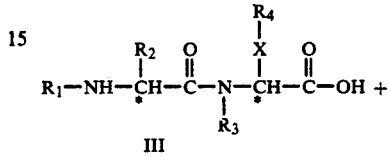

III

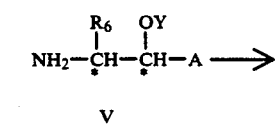

V

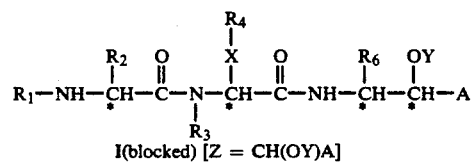

I(blocked) [Z = CH(OY)A]

Alternatively N-blocked tripeptide aldehydes of formula VI are prepared and reacted with a compound of formula VII where M⊕ is a metal such as sodium, potassium, lithium and the like to give compounds of formula I where Z is —CH(OH)A

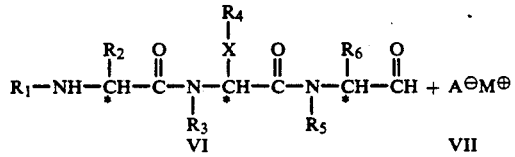

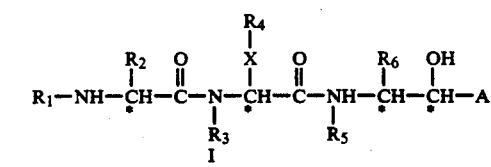

Preferably the tripeptide aldehydes of formula VI are reacted with trimethylsilyl derivatives of formula VIII in the presence or absence of tetrabutylammonium fluoride, cesium fluoride or an equivalent source of fluoride anion giving the O-trimethylsilyl derivatives of formula IX or the desilylated derivatives of formula IX.

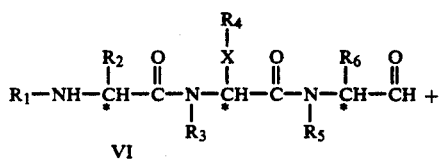

VI

VIII

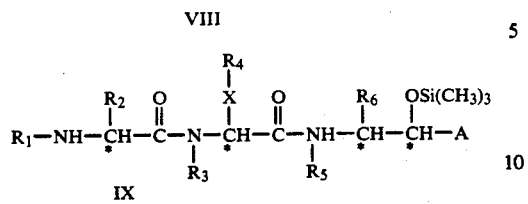

IX

Removal of the trimethylsilyl group under standard conditions such as treatment with dilute acid or tetrabutylammonium fluoride gives the compounds of formula I where Z is —CH(OH)A.

The intermediates of formula XI or XII are prepared by reacting an N-blocked-α-amino aldehyde of formula X wherein $R_9$ is t-butyloxycarbonyl, benzyloxycarbonyl, triphenylmethyl and the like with compounds of formula VII or VIII.

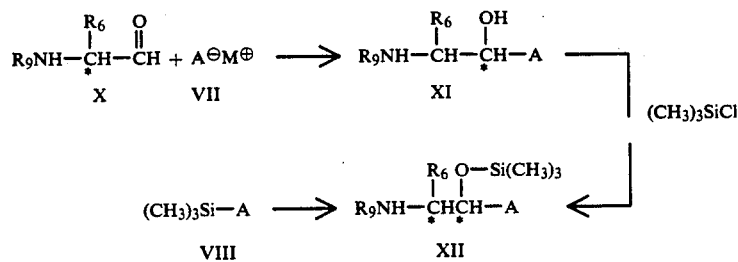

The most preferred compounds of X are those with the L (S configuration which give a pair of diastereomers on reaction with compound VII or VIII. The pair of diastereomers may be separated by chromatography on silica gel, and coupled to a peptide moiety of formula III as previously described.

As representative examples of the above process (Scheme A), 2-trimethylsilylthiazole 1 is reacted with L-t-butoxycarbonylphenylalanel 2 or L-t-butoxycarbonylleucinal 3 in dichloromethane to give diastereomers 4, 5 and 6, 7 respectively. Removal of the trimethylsilyl group with fluoride anion affords the free hydroxy compounds 4b 5b and 6b, 7b respectively. Separation of the diastereomers is carried out by chromatography. The most preferred diastereomers are (S)2(tert-butoxycarbonyl)amino-3-phenyl-(R)1-(2-thiazolyl)propan-1-ol 4b and (S)2-(tert-butoxycaronyl)amino-4-methyl-(R)1-(2-thiazolyl)pentan-1-ol 6b.

Scheme A

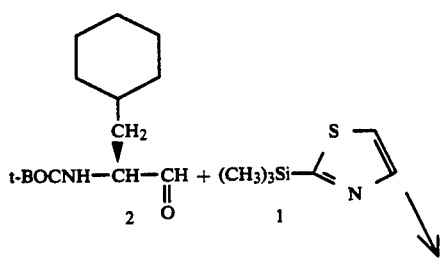

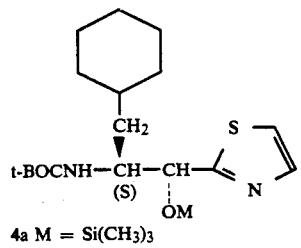

4a M = Si(CH₃)₃
4b M = H

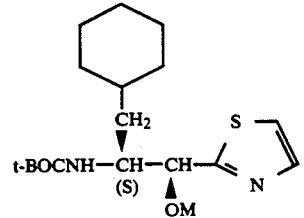

5a M = Si(CH₃)₃
5b M = H

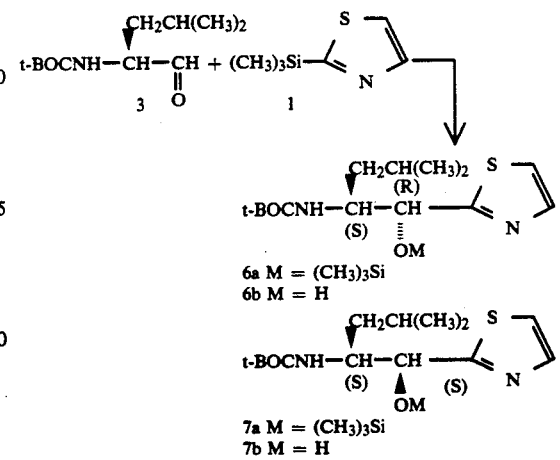

6a M = (CH₃)₃Si
6b M = H

7a M = (CH₃)₃Si
7b M = H

The compounds of formula I, where Z is —CHO are prepared by reduction of N-methyl-N-methoxy amides of the formula XIII with lithium aluminum hydride

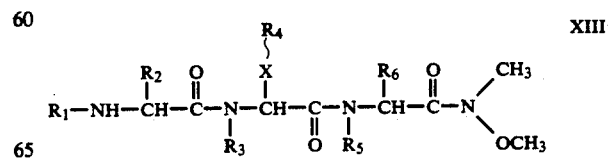

Intermediates of formula XVI may be prepared by reaction of Li a (where A is a moiety as previously defined) with N-methyl-N-methoxy amides of formula XIV to give the keto derivatives XV. Reduction of the keto derivative XV with hydrides such as sodium borohydride, lithium or potassium tri-sec-butylborohydride and triethylsilane gives the intermediates XVI as a pair of diastereomers. The amount of each diastereomer in the mixture represented by formula XVI depends on the structure of the hydride reducing reagent and reaction conditions. In general, lithium and potassium tri-sec-butylborohydrides give selectively diasteromer XVII.

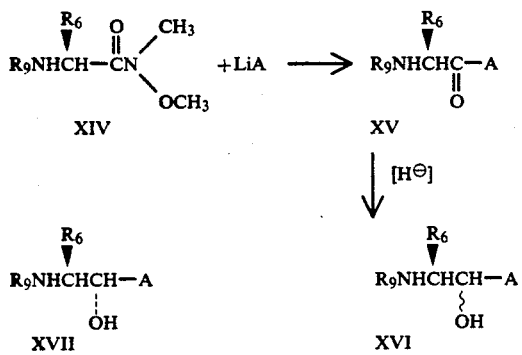

the compounds of formula I are active inhibitors of renin.

Renin is an endopeptidase which plays an important role in the control of blood pressure. The renin angiotension system is a multiregulated proteolytic cascade in which renin cleaves the protein substrate angiotensinogen to give angiotensin I. Angiotensin converting enzyme (ACE) catalyses the removal of the terminal dipeptide from the decapeptide angiotensin I to form angiotensin II which exhibits potent pressor activity.

Renin is an aspartyl protease with high substrate specificity and is the first proteolytic step in the renin-angiotensin system which is involved in the control of blood pressure.

Renin inhibitors have been shown to lower blood pressure in primates, [J. Hypertension, 1, 399 (1983), J. Hypertension 1 (suppl 2), 189 (1983)] and in man, [Lancet II, 1486 (1983), Trans. Assoc. Am. Physicians, 96, 365 (1983), J. Hypertension, 3, 653 (1985] and thus are potentially useful in the control of hypertension.

The novel compounds of formula I are new peptide renin inhibitors and are useful in the treatment of hypertension in warm-blooded animals, as established in the following test.

Radioimmunoassay Screen For Renin Inhibitors

The in vitro method for the screening of anti-renin compounds involves, first, angiotensin I generation, and second, the quantitation of the angiotensin I produced by radioimmunoassay.

Angiotensin I Generation

The incubation medium consisted of 20 μl of purified human plasma angiotensinogen (1); 40 μl of human kidney renin (2); 5 μl of phenylmethylsulfonyl fluoride; 10 μl of disodium EDTA (10 mM); 10 μl of antirenin compound ($5 \times 10^{-3}$, $5 \times 10^{-4}$, $5 \times 10^{-5}$) in dimethylformamide, or ethanol and a suitable amount of maleate buffer (77mM, pH 6.0) to make a final volume of 500 μl. The reaction mixture was incubated for 1 hour at 37° C. and the enzymatic reaction was stopped by placing the tube in ice-cold water. The angiotension I generated during the incubation was measured by a radioimmunoassay plasma renin activity kit (Clinical Assays, Inc.).

Radioimmunoassay Procedure

The incubation medium consisted of either 100 μl aliquots of the above reaction mixture or a standard amount of angiotensin I; 1000 μl of phosphate buffer (100 mM, pH7.6) and 100 μl of ($^{125}$I)angiotensin in a gamma-coat, tube. After three hours of incubation at room temperature, the tubes were decanted, and the radioactivity of each tube was determined in a gamma counter. Duplicate determinations were performed for each incubation. The results were expressed in ng of angiotensin I generated per ml of generation medium per hour of incubation (ng/AI/ml/hr), and the % of inhibition was obtained by the following: % inhibition=

$$100 - \left( \frac{\text{Renin activity in the presence of the test compound}}{\text{Renin activity without the test compound}} \times 100 \right).$$

The results of this test on representative compounds of this invention appear in Table I, expressed as an IC$_{50}$.

(1) The human plasma angiotensinogen derived from the blood of a woman receiving oral contraceptive pills was purified by chromatography on a pepstatin-aminohexyl-agarose column.

(2) Human renin was prepared from human kidney.

TABLE I

| Compound | Molar Concentration | % Renin Inhibition | IC$_{50}$ Molar Concentration |
|---|---|---|---|
| N-[(Phenylmethoxy)carbonyl]-L-phenylalanyl-L-2-(2-methyl-propoxy)glycyl-(1R,2S)-2-amino-3-phenyl-1-(2-thiazolyl)-propan-1-ol | $1 \times 10^{-4}$ $1 \times 10^{-5}$ $1 \times 10^{-6}$ | 85.0 84.6 76.2 | $4.7 \times 10^{-7}$ |
| N-[(Phenylmethoxy)carbonyl]-L-phenylalanyl-D-2-(2-methyl-propoxy)glycyl-(1R,2S)-2-amino-3-phenyl-1-(2-thiazolyl)-propan-1-ol | $1 \times 10^{-4}$ $1 \times 10^{-5}$ $1 \times 10^{-6}$ | 74.6 69.2 41.0 | |
| N-[Phenylmethoxy)carbonyl-L-phenylalanyl-L-2-(cyclohexyloxy)glycl-(1R,2S)-2-amino-4-methyl-1-(2-thiazolyl)-pentan-1-ol | | | $8.5 \times 10^{-6}$ |
| N-[N-(Phenylmethoxy)carbonyl-L-phenylalanyl-L-2-(1-methyl-ethoxy)glycyl]-(S)2-amino-4-methyl-(R)-1-(2-thiazolyl)-pentan-1-ol | | | $2.8 \times 10^{-7}$ |
| N-[(Phenylmethoxy)carbonyl]-phenylalanyl-L-2-(2-methyl-propoxy)glycyl-(1R,2S)-2-amino-3-cyclohexyl-1-(2-thiazolyl)propan-1-ol | | | $8.7 \times 10^{-8}$ |
| N-[Phenylmethoxy)carbonyl]-L-phenylalanyl-D-2-(2-methyl-propoxy)glycyl-(1R,2S)-2-amino-3-cyclohexyl-1-(2-thiazolyl)propan-1-ol | | | $1.1 \times 10^{-5}$ |
| N-[N-(Benzyloxycarbonyl)-L-phenylalanyl-L-2-(2-methylpropoxy)glycyl]-(S)2-amino-4-methyl-(R)1-(1-methyl-1H-1,2,4-triazol-5-yl)-pentan-1-ol | $1 \times 10^{-4}$ | 32 | |
| N-[(Phenylmethoxy)carbonyl]-L-phenylalanyl-N-[(S)-1-formyl-2-phenylethyl]-L-2-(2-methylpropoxy)- | $10^{-4}$ $10^{-5}$ | 66 59 | |

TABLE I-continued

| Compound | Molar Concentration | % Renin Inhibition | IC$_{50}$ Molar Concentration |
|---|---|---|---|
| glycinamide N-[(Phenylmethoxy)carbonyl]-L-phenylalanyl-N-[(S)-1-formyl-3-methylbutyl]-L-2-(2-methoxypropoxy)-glycinamide | $10^{-4}$ $10^{-5}$ | 70 50 | |
| N-[(Phenylmethoxy)carbonyl]-L-phenylalanyl-N-[(S)-1-formyl-3-methylbutyl]-L-2-(1-methylethoxy)-glycinamide | | | $1 \times 10^{-5}$ |
| N-[N-(tert-Butoxycarbonyl)-L-phenylalanyl-L-leucyl]-(S)2-amino-4-methyl-(R)1-(2-thienyl)pentan-1-ol | | | $4.5 \times 10^{-6}$ |
| N-[N-Benzyloxycarbonyl)-L-phenylalanyl-L-2(1-methylethoxy)glycyl]-(S)2-amino-4-methyl-(R)1-(2-thiazolyl)-pentan-1-ol | | | $2.8 \times 10^{-7}$ |
| N-[N-(Phenylmethoxy)-carbonyl-L-phenylalanyl-D-2-(1-methylethoxy)-glycyl]-(S)2-amino-3-cyclohexyl-(R)1-(2-pyridinyl)propan-1-ol. | | | $1 \times 10^{-6}$ |
| N-[N-(Phenylmethoxy)-carbonyl-L-phenylalanyl-D-2-(isopropylthio)-glycyl]-(S)2-amino-4-methyl-(R)-1-(2-thiazolyl)pentan-1-ol. | $10^{-4}$ | 25% | |
| N-[N-(Phenylmethoxy)-carbonyl-L-phenylalanyl-D-2-(1-methylethoxy)-glycyl]-(S)2-amino-3-cyclohexyl-(R)1-(2-thiazolyl)propan-1-ol. | | | $8.8 \times 10^{-6}$ |
| N-[N-(Phenylmethoxy)-carbonyl-L-phenylalanyl-D-2-(2-methylpropoxy)-glycyl]-(S)2-amino-3-cyclohexyl(R)1-(2-pyridinyl)propan-1-ol. | | | $2.9 \times 10^{-5}$ |
| N-[N-(phenylmethoxy)-carbonyl-L-phenylalanyl-D-2-(isopropylthio)glycyl]-(S)2-amino-3-cyclohexyl-(R)1-(2-pyridinyl)propan-1-ol. | | | $1.6 \times 10^{-5}$ |
| N-[N-(Phenylmethoxy)carbonyl-L-phenylalanyl-L-2-(1-methylethoxy)glycyl]-(S)2-amino-3-cyclohexyl-(R)-1-(2-pyridinyl)-propan-1-ol. | | | $2.4 \times 10^{-8}$ |
| N-[N-(Phenylmethoxy)-carbonyl-L-phenylalanyl-L-2-(isopropylthio)glycyl]-(S)2-amino-4-methyl-(R)-1-(2-thiazolyl)pentan-1-ol. | | | $1.4 \times 10^{-5}$ |
| N-[N-(Phenylmethoxy)-carbonyl-L-phenylalanyl-L-2-(1-methylethoxy)glycyl]-(S)-2-amino-3-cyclohexyl-(R)-1-(2-thiazolyl)-propan-1-ol. | | | $1.0 \times 10^{-9}$ |
| N-[N-(Phenylmethoxy)-carbonyl-L-2-(2-methylpropoxy)glycyl]-(S)2-amino-3-cyclohexyl(R)1-(2-pyridinyl)propan-1-ol. | | | $1.6 \times 10^{-7}$ |
| N-[N-(Phenylmethoxy)-carbonyl-L-phenylalanyl-L-2-(isopropylthio)glycyl]-(S)2-amino-3-cyclohexyl-(R)1-(2-pyridinyl)-propan-1-ol. | | | $4.6 \times 10^{-8}$ |
| N-[N-(tert-Butoxycarbonyl)-L-phenylalanyl-L-leucyl]-(S)2-amino-3-cyclohexyl-(R)1-(2-furanyl)propan-1-ol. | | | $2.4 \times 10^{-8}$ |

The novel compounds of the present invention have been found to be highly useful for lowering elevated blood pressure in mammals when administered in amounts ranging from about 5 mg to about 50 mg/kg of body weight per day.

The compounds of this invention are preferably administered by a parenteral route such as intravenous, intramuscular or subcutaneous, but may be administered orally is desired.

Compositions, according to the present invention, having the desired clarity, stability and adaptability for parenteral use are obtained by dissolving from 0.10% to 10% by weight of active compound in a vehicle consisting of a polyhydric aliphatic alcohol or mixtures of such alcohols. Especially satisfactory are glycerin, propylene glycol and polyethylene glycols. Although various mixtures of polyethylene glycols may be used, it is preferred to use a mixture having an average molecular weight of from about 200 to about 400.

In addition to the active compound, the parenteral solutions may also contain various preservatives to prevent bacterial and fungal contamination as well antioxidants to promote stability.

For intramuscular injection, the preferred concentration of active compound is 0.25 to 0.50 mg/ml of the finished compositions.

The novel compounds of this invention are equally adapted to intravenous administration when diluted with water or diluents employed in intravenous therapy such as isotonic glucose. For intravenous use, initial concentrations down to about 0.05 to 0.25 mg/ml of active compound are satisfactory.

The following reference examples illustrate the preparation of intermediate compounds useful in out invention.

REFERENCE EXAMPLE 1

N$^{\alpha}$-[(Phenylmethoxy)carbonyl]-L-phenylalaninamide

An 18 g portion of N$^{\alpha}$-[(phenylmethoxy)carbonyl]-L-phenylalanine and 6.6 ml of N-methylmorpholine were dissolved in 150 ml of tetrahydrofuran and stirred at 31 10° C. as 8.04 ml of isobutylchloroformate was added. After 1 minute, ammonia gas was bubbled through the mixture until it was saturated. The mixture was stirred an additional 30 minutes and then poured into ice-water. The white solid was collected, giving 16.76 g of the desired compound, mp 164°–165° C.

REFERENCE EXAMPLE 2

N-[(Phenylmethoxy)carbonyl)-L-phenylalanyl-D, L-2-hydroxyglycine

A solution of 16.8 g of N$^{\alpha}$-[phenylmethoxy)carbonyl]-L-phenylalaninamide, and 6.06 g of glyoxylic acid in 90 ml of acetone was refluxed for 6 hours, then poured into ice-water and stirred. The resulting white solid was collected and dried, giving 16.8 g of the desired compound, mp 137°–141° C.

REFERENCE EXAMPLE 3

N-[(Phenylmethoxy)carbonyl]-L-phenylalanyl-D,L-2-(2-methylpropoxy)glycine, 2-methypropyl ester A mixture of 9.2 g of N-[(phenylmethoxy)carbonyl]-L-phenylalanyl-D, L-2-hydroxyglycine in 120 ml of isobutanol containing 0.5 ml of concentrated sulfuric acid was stirred for 30 minutes, then warmed on a steam bath for 4 hours, cooled and poured into cold saturated sodium bicarbonate solution. This mixture was extracted three times with ethyl acetate. The extracts were combined, dried, filtered and evaporated, giving a solid which was recrystallized from ethanol, giving 7.3 g of the desired compound. After recrystallization from aqueous ethanol the solid melted at 120°–123°C.

REFERENCE EXAMPLE 4

N-[(Phenylmethoxy)carbonyl]-L-phenylalanyl-D,L-2-(2-methylpropoxy)glycine

A solution comprising 7.3 g of N-[(phenylmethyoxy)carbonyl]-L-phenylalanyl-D,L-2-(2-methylpropoxy)glycine, 2-methylpropyl ester, 15 ml of 1N sodium hydroxide and 150 ml of methanol was stirred for 15 hours then acidified with 3N hydrochloric acid and evaporated to an oil. The addition of water produced a solid which was collected, giving 6.1 g of the desired compound, mp 99°–109° C.

REFERENCE EXAMPLE 5

N-Methoxy-N-methyl-L-phenylalaninamide, trifluoroacetate

To 21.75 g of N-methoxy-N-methyl-L-t-butoxycarbonyl phenylalaninamide, chilled in an ice-methanol bath, was added with stirring, 50 ml of trifluoroacetic acid. After three hours the solvent was removed in vacuo. Ether was added twice and the solvent removed, than 100 ml of ether was added and the mixture was chilled. The resulting solid was collected, washed with the ether and air dried, giving 19 g of the desired compound as crystals, mp 123°–124° C.

REFERENCE EXAMPLE 6

N-[(Phenylmethoxy)carbonyl]-L-phenylalanyl-L-2-(2-methyl propoxy)glycol-N-methoxy-N-methyl-L-phenylalaninamide, and N-[(Phenylmethoxy)carbonyl]-L-phenylalanyl-D-2-(2-methylpropoxy)glycyl-N-methoxy-N-methyl-L-phenylalaninamide To a solution of 3 g of N-[(phenylmethoxy)carbonyl]-L-phenylalanyl-D,L-2-(2-methylpropoxy)glycine, 1.73 g of 2-ethoxy-1(2H)-quinolinecarboxylic acid, ethyl ester and 70 ml of dichloromethane, was added a solution of 2.25 of N-methoxy-N-methyl-L-phenylalaninamide trifluoroacetate and 1.2 ml of triethylamine in 35 ml of dichloromethane. This mixture was stirred for 20 hours and then evaporated. Chloroform was added to the residual oil and this solution was then washed three times with 3N hydrochloric acid, three times with saturated sodium bicarbonate solution and three times with saturated sodium chloride solution, then dried, filtered and evaporated giving 4.8 g of an oil. This oil was combined with 5.7 g of oil prepared in the same manner, placed on a 30×2 cm silica gel column and eluted with ethyl acetate:hexane (1:1).

The second fraction gave 1.16 of N-[(phenylmethoxy)carbonyl]-L-phenylalanyl-L-2-(2-methylpropoxy)glycyl-N-methoxy-N-methyl-L-phenylalaninamide as an amorphous solid, Rf=0.55 [ethyl acetate-hexane (1:1)]; $[\alpha]_D^{26} = -11 \pm 3°$(c, 0.35, methanol).

After eliminating intermediate fractions the second compound N-[(phenylmethoxy)carbonyl]-L-phenylalanyl-D-2-(2-methylpropoxy)glycyl-N-methoxy-N-methyl-L-phenylalaninamide was collected as 1.25 g of amorphous solid, Rf=0.33 [ethyl acetate-hexane (1:1)]; $[\alpha]_D^{26} = 0°$ (c, 0.3, methanol).

REFERENCE EXAMPLE 7

N-Methoxy-N-methoxy-L-leucinamide, trifluoroacetate

A mixture of 2 g of N-methoxy-N-methyl-t-butoxycarbonyl-L-leucinamide and 20 ml of trifluoroacetate acid:- water (9:1) was stirred at 0° C. for 4 hours. The solvent was removed in vacuo and the oily residue triturated with ether. The resulting solid was collected and air dried, giving 1.7 g of the desired compound as a white solid, mp 96°–98° C.

REFERENCE EXAMPLE 8

N-[(Phenylmethoxy)carbonyl]-L-phenylalanyl-2-L-(2-methylpropoxy)glycyl-N-methoxy-N-methyl-L-leucinamide and N-[(Phenylmethoxy)carbonyl]-L-phenylalanyl-D-2-(2-methylpropoxy)glycyl-N-methoxy-N-methyl-L-leucinamide To a solution of 3 g of N-[(phenylmethoxy)carbonyl]-L-phenylalanyl-(D,L)-2-(2-methylpropoxy)glycine, 1.73 g of 2-ethoxy-1(2H)-quinolinecarboxylic acid, ethyl ester and 70 ml of dichloromethane, was added a solution of 2.08 g of N-methoxy-N-methyl-L-leucinamide, trifluoroacetate and 1.2 ml of triethylamine in 35 ml of dichloromethane. This mixture was stirred for 17 hours and then evaporated. Chloroform was added to the residual oil and the resulting solution was washed three times each with 3N hydrochloric acid, saturated sodium bicarbonate solution and saturated sodium chloride solution, then dried, filtered and evaporated. The residual oil was placed on a silica gel column (30×2 cm) and eluted with ethyl acetate:hexane (1:1) collecting 25 ml fractions. Fractions 8–10 were combined and evaporated, giving 0.76 g of N-[phenylmethoxy)carbonyl]-L-phenylalanyl-L-2-( 2-methylpropoxy)glycyl-N-methoxy-N-methyl-1-L-leucinamide as an oil, Rf=0.60 [ethyl acetate-hexane (1:1)]; $[\alpha]_D^{26} = -29° \pm 3°$(c, 0.37, methanol).

Fractions 12–17 were combined and evaporated, giving 1.16 g of N-[(phenylmethoxy)carbonyl]-L-phenylalanyl-D-2-(2-methylpropoxy)glycyl-N-methoxy-N-methyl-L-leucinamide as an oil, Rf=0.43 [ethyl acetate-hexane (1:1)]; $[\alpha]_D^{26} = -7° \pm 2°$(c, 0.635, methanol).

REFERENCE EXAMPLE 9

N-[(Phenylmethoxy)carbonyl]-L-phenylalanyl-D,L-2-methoxyglycine, methyl ester

A solution of 0.4 g of N-[(phenylmethoxy)carbonyl]-L-phenylalanyl-D,L-2-hydroxyglycine, 50 ml of methanol and 0.3 ml of concentrated sulfuric acid was stirred for 2 days and then poured into cold saturated sodium bicarbonate solution. The resulting suspension was extracted with ethyl acetate. The extract was dried, filtered and evaporated. The residue was recrystallized from aqueous methanol, giving 0.25 g of the desired compound, mp 128°-132° C.

REFERENCE EXAMPLE 10

N-[(Phenylmethoxy)carbonyl]-L-phenylalanyl-D,L-2-methoxyglycine

A solution of 0.47 g of D,L-2-methoxy-N-[N-[(phenylmethoxy)carbonyl]-L-phenylalanyl glycine, methyl ester in 15 ml of methanol and 1.2 ml of 1N sodium hydroxide was stirred for 1 hour, then acidified and evaporated. Water was added to the residue. The resulting solid was recrystallized from aqueous methanol, giving 0.2 g of the desired compound as a solid, mp 75°-90° C.

REFERENCE EXAMPLE 11

N-[(Phenylmethoxy)carbonyl]-L-phenylalanyl-D,L-2-ethoxyglycine, ethyl ester

A solution of 3.7 g of N-[(phenylmethoxy)carbonyl]-L-phenylalanyl-D,L-2-hydroxyglycine in 50 ml of ethanol and 0.3 ml of concentrated sulfuric acid was stirred for 18 hours and then refluxed for 48 hours. The clear solution was poured into cold saturated sodium bicarbonate solution and then extracted three times with ethyl acetate. The extracts were combined, washed with water, dried, filtered and evaporated. The oily residue solidified and was recrystallized from chloroform/hexane, giving 1.7 g of the desired compound, mp 99°-110° C. (dec.).

REFERENCE EXAMPLE 12

N-[(Phenylmethoxy)carbonyl]-L-phenylalanyl-D,L-2-ethoxyglycine

A solution of 1.5 of N-[(phenylmethoxy)carbonyl]-L-phenylalanyl-D,L-2-ethoxyglycine, ethyl ester, 50 ml of methanol and 3.5 ml of 1N sodium hydroxide was stirred overnight, then acidified with 6N hydrochloric acid and evaporated to an oil. Water was added and the mixture stirred until the oil solidified. One recrystallization from chloroform/hexane gave 1 g of the desired compound as a white solid, mp 138°-143° C. (dec.).

REFERENCE EXAMPLE 13

N-[(Phenylmethoxy)carbonyl]-L-phenylalanyl-D,L-2-(1-methylethoxy)glycine, 1-methylethyl ester A mixture of 3.7 g of N-[(phenylmethoxy)carbonyl]-L-phenylalanyl-D,L-2-hydroxyglycine, 50 ml of isopropanol and 0.3 ml of concentrated sulfuric acid was stirred at room temperature for 17 hours, warmed on a steam bath for ½ hour and then stirred at room temperature for 48 hours. This mixture was filtered and the filtrate evaporated to an oil which solidified after washing with sodium bicarbonate solution and water. This solid was chromatographed on a 30×2 cm silica gel column, eluting with ethyl acetate:hexane (1:1), collecting 25 ml fractions. The first two fractions were combined and evaporated, giving 0.6 g of the desired compound, mp 103°-111° C.; Rf=0.87 [ethyl acetate-hexane (1:1)]; $[\alpha]_D^{26} = +5° \pm 1°$(c, 1.1 methanol).

REFERENCE EXAMPLE 14

N-[(Phenylmethoxy)carbonyl]-L-phenylalanyl-D,L-2-(1-methylethoxy)glycine

A solution of 1.4 g of N-[(phenylmethoxy)carbonyl]-L-phenylalanyl-D,L-2-(1-methylethoxy)glycine,1-methylethyl ester, 45 ml of methanol and 3 ml of 1N sodium hydroxide was stirred for 20 hours, then acidified with 6N hydrochloric acid and evaporated. Water was added to the residue and the mixture was stirred until a white solid separated. This solid was recrystallized from chloroform/hexane, giving 0.7 g of the desired compound as a white solid, mp 122°-128° C. (dec.).

REFERENCE EXAMPLE 15

N[(Phenylmethoxy)carbonyl]-L-phenylalanyl-L-2-(1-methylethoxy)glycyl-N-methoxy-N-methyl-L-leucinamide A solution of 1.37 g of N-methoxy-N-methyl-L-leucinamide, trifluoroacetate, 0.7 ml of triethylamine and 10 ml of dichloromethane was added to a solution of 1.9 g of N-[(phenylmethoxy)carbonyl]-L-phenylalanyl-D, L-2-(1-methylethoxy)glycine and 1.14 g of 2-ethoxy-1(2H)-quinolinecarboxylic acid, ethyl ester in 25 ml of dichloromethane. This mixture was stirred for 18 hours and then evaporated to an oil .The oil was washed three times each with 3N hydrochloric acid, sodium bicarbonate solution and sodium chloride solution, dried, filtered and evaporated. The oily residue was chromatographed on a 40×3 cm silica gel column eluting with ethyl acetate:hexane, collecting 50 ml fractions. Fractions 4-6 were combined and evaporated, giving 0.9 g of the desired compound as an amorphous solid, Rf=0.5 [ethyl acetate-hexane (1:1); $[\alpha]_D^{26} = \pm 45° \pm 2°$(c, 0.645, methanol).

N-[(Phenylmethoxy)carbonyl]-L-phenylalanyl-D,L-2-(phenylmethoxy)glycine, phenylmethyl ester A suspension of 37 g of N-[(phenylmethoxy)carbonyl]-L-phenylalanyl-D, L-2-hydroxyglycine in 250 ml of benzyl alcohol was treated with 3 ml of concentrated sulfuric acid, heated on a steam bath for 1.5 hours, diluted with hexane and chilled. The solid was collected, washed with ether and recrystallized from ethyl acetate/ether, giving 27.5 of the desired compound, mp 130°-140° C.

REFERENCE EXAMPLE 27

N-[(Phenylmethoxy)carbonyl]-L-phenylalanyl-D,L-2-(phenylmethoxy)glycine

To a suspension of 29.9 g of N-[(phenylmethoxy)carbonyl]-L-phenylalanyl-D, L-2-(phenylmethoxy)glycine, phenylmethyl ester in 500 ml of methanol was added 60 ml of 1N sodium hydroxide with stirring. Stirring was continued for 1.5 hours then the mixture was heated to boiling to produce solution, filtered and the filtrate was acidified to pH 1.5 with 1N hydrochloric acid followed by the addition of water to the cloud point. The resulting suspension was cooled and the solid was collected and dried, giving 22.34 g of the desired compound, mp 139°-142° C.

REFERENCE EXAMPLE 18

(−)-N-[(Phenylmethoxy)carbonyl]-L-phenylalanyl-[R-(or S)]-2-(phenylmethoxy)glycyl-N-methoxy-N-methyl-L-phenylalaninamide and (+)-N-[(Phenylmethoxy)carbonyl]-L-phenylalanyl-[R(or S)]-2-(phenylmethoxy)glycyl-N-methoxy-N-methyl-L-phenylalaninamide To a suspension of 12.47 g of N-[(phenylmethoxy)carbonyl]-L-phenylalanyl-D,L-2-(phenylmethoxy)glycine in 140 ml of dichloromethane was added 7.4 g of 2-ethoxy-1(2H)-quinolinecarboxylic acid, ethyl ester. The mixture was stirred 5 minutes, then a solution of 8.7 g of N-methoxy-N-methyl1-phenylalaninamide, trifluoroacetate and 3.8 ml of triethylamine in 50 ml of dichloromethane was added and stirring was continued overnight. The solution was concentrated to an oil which was dissolved in 100 ml of ethyl acetate, washed with 2N hydrochloride acid, sodium bicarbonate solution and brine, dried, filtered and concentrated to an oil.

This oil, in two batches, was chromatographed by HPLC on a Waters Prep 520 column (silica gel) with ethyl acetate:dichloromethane (1:4) as eluent. After 10 holdback volumes, the least polar component was eluted with ethyl acetate:dichloromethane (1:1). These fractions were concentrated in vacuo and the residue was crystallized first from dichloromethane/diisopropyl ether, then from ethyl acetate/diisopropyl ether, giving 4.0 g of (+)-N-[(phenylmethoxy)carbonyl]-L-phenylalanyl-[R(or S)]-2-(phenylmethoxy)glycyl-N-methoxy-N-methyl-L-phenylalaninamide, mp 135°–140° C.; $[\alpha]_D^{26} = +17° \pm 0.5°$(c, 0.12, chloroform).

The fractions containing the more polar component were concentrated in vacuo and the residue crystallized from diisopropyl ether/dichloromethane, giving 5.73 g of (−)-N-[(phenylmethoxy)carbonyl]-L-phenylalanyl-[R(or S)]-2-(phenylmethoxy)glycyl-N-methoxy-N-methyl-L-phenylalaninamide, mp 138°–139° C.; $[\alpha]_D^{26} = -30° \pm 1°$(c, 1.385, methanol).

REFERENCE EXAMPLE 19

N-[(Phenylmethoxy)carbonyl]-L-phenylalanyl-D-2-(phenylmethoxy)glycyl-N-methoxy-N-methyl-L-leucinamide and N-[(Phenylmethoxy)carbonyl]-L-phenylalanyl-L-2-(phenylmethoxy)glycyl-N-methoxy-N-methyl-L-leucinamide To a suspension of 13.9 g of N-[(phenylmethoxy)carbonyl]-L-phenylalanyl-D,L-2-(phenylmethoxy)glycine in 60 ml of dichloromethane was added 7.4 g of 2-ethoxy-1(2H)-quinolinecarboxylic acid, ethyl ester. After the solution became complete, a solution of 8.8 g of N-methoxy-N-methyl-L-leucinamide, trifluoroacetate and 4.1 ml of triethylamine in 58 ml of dichloromethane was added. This solution was stirred overnight, then washed three times each with 60 ml portions of 2N hydrochloric acid, 1N sodium bicarbonate and sodium chloride solution. The organic layer was dried, filtered through a thin pad of dichloromethane washed hydrous magnesium silicate and concentrated in vacuo, giving 16.1 g of an oil. This oil was chromatographed by HPLC on a Water Prep 520 column (silica gel) with ethyl acetate:dichloromethane (1:4) as solvent. Two components (A & B) were isolated form the two main peaks.

Fractions containing component A were combined and concentrated in vacuo, giving an oil which was crystallized from ether, giving 4.46 g of N-[(phenylmethoxy)carbonyl]-L-phenylalanyl-L-2-(phenylmethoxy)glycyl-N-methoxy-N-methyl-L-leucinamide, as white crystals, mp 88°–89° C.; $[\alpha]_D^{26} = -39° \pm 1°$(c, 0.96, methanol).

Fractions containing component B were combined and the solvent removed in vacuo, giving 7.1 g of N-[(phenylmethoxy)carbonyl]-L-phenylalanyl-D-2-(phenylmethoxy)glycyl-N-methoxy-N-methyl-L-leucinamide as an oil.

REFERENCE EXAMPLE 20

N-[(Phenylmethoxy)carbonyl]-L-phenylalanyl-D,L-2-(cyclohexylmethoxy)glycine, cyclohexylmethyl ester A mixture of 30 g of N-[(phenylmethoxy)carbonyl]-L-2-hydroxyglycine, 100 g of cyclohexylmethanol and 2.4 ml of concentrated sulfuric acid was stirred and heated at 90°–100° C. for 4 hours. The mixture was then cooled and stirred overnight at room temperature. Hexane was added and the solid collected, washed with hexane, cold water, saturated sodium bicarbonate solution and again with water. This solid was chromatographed on a silica gel column, eluting with dichloromethane:ethyl acetate (98:2) . The product fractions were combined, evaporated and the residue triturated with hexane. Filtration gave 19.1 g of the desired compound as white crystals, mp 122°–125° C.; $[\alpha]_D^{26} = -8° \pm 1°$(c, 1.14, acetone).

REFERENCE EXAMPLE 21

N-[(Phenylmethoxy)carbonyl]-L-phenylalanyl-D,L-2-(cyclohexyloxy)glycine, cyclohexyl ester A mixture of 3.7 g of N-[(phenylmethoxy)carbonyl]-L-phenylalanyl-D,L-2-hydroxyglycine, 50 ml of cyclohexanol and 0.3 ml of concentrated sulfuric acid was heated on a steam bath for 2 hours, then cooled overnight. A 50 ml portion of ethyl acetate was added, the mixture washed with sodium bicarbonate solution, brine and dried. The solution was filtered through a thin pad of hydrous magnesium silicate and the filtrate concentrated in vacuo to an oil. The oil was crystallized from hexane with chilling and recrystallized from methanol, giving 2.2 g of the desired compound as white crystals mp 106°–118° C.

REFERENCE EXAMPLE 22

N-[(Phenylmethoxy)carbonyl]-L-phenylalanyl-D,L-2-(cyclohexyloxy)glycine

To a solution of 4.5 g of N-[(phenylmethoxy)carbonyl]-L-phenylalanyl-D,L-2-(cyclohexyloxy)glycine, cyclohexyl ester in 40 ml of warm methanol was added 9.2 ml of 1N sodium hydroxide. This mixture was stirred 2 hours, then acidified with 5 ml of 2N hydrochloric acid and diluted with water to the cloud point. The mixture was diluted further with water, stirred, chilled and the solid collected. This solid was recrystallized form chloroform/hexane, giving 3.28 g of the desired compound, mp 119°–121° C.; $[\alpha]_D^{26} = -3°$(c, 0.539, methanol).

REFERENCE EXAMPLE 23

5-[(S)2-tert-Butoxycarbonylamino-(R,S)1-hydroxy-4-methylpentyl]-2-thiopenecarboxylic acid A solution of 3.9 ml of dry distilled diisopropylamine in 10 ml of dry tetrahydrofuran under argon was chilled to −70° C. and to the solution was added 11.81 ml of 2.36 M n-butyllithium in tetrahydrofuran via syringe. The solution was stirred for 20 minutes and then a solution of 1.7 g of 2-thiopenecarboxylic acid in 10 ml of tetrahydrofuran was added (via syringe). After stirring for 40 minutes at −70° C., a solution of 1.5 g of N-tert-butoxycarbonyl-L-leucinal in 10 ml of tetrahydrofuran was added. The mixture was stirred at −70° C. for one hour and quenched with 10% ammonium chloride solution. The mixture was allowed to warm to room temperature and the solvent under vacuum. The residue was extracted with ether. The combined ether extracts were washed with 1N hydrochloric acid, saturated sodium bicarbonate solution and with saturated sodium chloride solution and dried. The solvent was removed under vacuum and the residue chromatographed an a silica gel column with hexane-ethylacetate-acetic acid (1:1:0.002) as eluent. The fractions containing product were combined and the solvent removed to give 0.28 g of gum: Rf 0.36 on TLC (silica gel) with hexane-ethyl acetate-acetic acid(1:1:0.002) as solvent.

REFERENCE EXAMPLE 24

(S)2-tert-Butoxycarbonylamino-4-methyl-(R,S)1-(2-furanyl)-pentan-1-ol

To 0.545 ml of furan in 10 ml of dry tetrahydrofuran under argon cooled to −20° C. was added 0.35 ml of 2.36 M n-butyllithium in hexane. The solution was allowed to warm to 10° C. and stirred for 2 hours. The solution was chilled to −70° C. (dry ice-acetone) and 1.70 g of N-t-butoxycarbonyl-L-leucinal in 10 ml of tetrahydrofuran was added. After 1 hour at −70° C., 10 ml of 10% ammonium chloride was added. The mixture was concentrated under vacuum, diluted with water and extracted with ether. The combined ether extracts were dried and concentrated. The residue was purified twice by thick layer chromatography on silica gel pates to give 0.20 g of product as a gum; RF 0.22 on thin layer chromatography (silica gel) with hexane-ethyl acetate (4:1) as solvent.

REFERENCE EXAMPLE 25

(S)2-tert-Butoxycarbonylamino-4-methyl-(R,S)-1-(2-thienyl)-pentan-1-ol

To a solution of 1.4 g of thiopene in 20 ml of dry tetrahydrofuran under argon was added 7.05 ml of 2.36 M n-butyllithium in tetrahydrofuran. The solution was stirred at room temperature for 45 minutes and then cooled to −70° C. (dry-ice acetone bath). A solution of 1.79 g of N-tert-butoxycarbonyl-L-leucinal in 10 ml of dry tetrahydrofuran was added via syringe. The mixture was stirred (—68° C.) for one hour and quenched with 10% ammonium chloride solution. After warming to room temperature, the solvent (tetrahydrofuran) was removed under vacuum. The residual aqueous mixture was extracted with ether. The combined ether extracts were washed with 50 ml of 1N hydrochloric acid, saturated sodium bicarbonate solution, saturated sodium chloride solution and dried. The solvent was removed and the residue chromatographed on a silica gel column with hexane-ethyl acetate (gradient elution) as solvent. The product was eluted with hexane-ethyl acetate (4:1). The fractions containing product were combined and the solvent removed under vacuum to give 1.15 g of gum; RF 0.34 on TLC (silica gel) with hexane-ethyl acetate (4:1).

REFERENCE EXAMPLE 26

5-[(S)2-Benzyloxycarbonylamino-(R,S)1-hydroxy-4-methylpentyl]-2-thiophenecarboxylic acid To a solution of 3.74 ml of dry distilled diisopropylamine in 10 ml of dry tetrahydrofuran at −70° C. under argon was added 11.33 ml of 2.36 M n-butyllithium in tetrahydrofuran via a syringe. After stirring 20 minutes, a solution of 1.71 g of 2-thiophenecarboxylic acid in 10 ml of tetrahydrofuran was added via a syringe. The mixture was stirred at −70° C. for 40 minutes and then 1.666 g of N-tert-butoxycarbonyl-L-leucinal in 10 ml of tetrahydrofuran was added. The solution was stirred at −70° C. for 1 hour and quenched with 10% ammonium chloride solution. The mixture was allowed to warm to room temperature and the tetrahydrofuran removed under vacuum. The residual aqueous mixture was extracted with ether and the combined ether extracts washed with 1N hydrochloric acid, and saturated sodium chloride solution. The extract was dried and the solvent removed. The residue was chromatographed on a silica gel column with hexane:ethyl acetate (1:1) containing 0.5% acetic acid. The fractions containing product were combined to give 0.23 g of crystals, mp 113°–117° C. Mass Spec. (FAB-low res.) 378 (M+H)

Anal. Calcd. For $C_{19}H_{23}NSO_5$: C, 60.5; H, 6.1; N, 3.7; Found: C, 60.5; H, 6.5; N, 4.0.

REFERENCE EXAMPLE 27

(S)2-Amino-4-methyl-(R)1-(2-thiazolyl)-pentan-1-ol

2Trimethylsilylthiazole [A. Medici et al., Chem. Com. 655(1981)] was prepared as follows: To a one liter 3-necked flask, equipped with two rubber septa, low temperature (−100° C.) thermometer and a magnetic stirrer and dried with a heat gum and a stream of dry nitrogen, was added via syringe 150 ml of freshly opened diethyl ether. A 32.8 g portion of 2-bromothiazole was added followed by another 50 ml of ether. The mixture was cooled to −65° C. in a dry ice-isopropanol bath and 87 ml of 2.3M n-butyllithium in hexane was very slowly added using a 50 ml syringe equipped with a long NO. 18 needle, while stirring and keeping the temperature below −50° C. The resulting dark brown solution was stirred at −65° C. for 1 hour and then treated with 25.4 ml of trimethylsilyl chloride via a syringe. The mixture was stirred for 30 minutes each at −60° C., −30° C. and 0° C. The mixture was washed with 200 ml of 0.5M sodium bicarbonate, then brine, dried, treated with charcoal, filtered on a bed of hydrous magnesium silicate and concentrated to an oil. The oil was slowly and carefully fractionated at a 10 cm Vigreux column, giving 18 g of 2-trimethylsilyl thiazole as a colorless oil, bp 55°–60° C.

To a solution of 10.8 g of t-butoxycarbonyl-L-leucinal in 40 of dichloromethane was added 9.4 g of 2-trimethylsilyl thiazole in 10 ml of dichloromethane. The reaction was allowed to stand for 48 hours, then was cooled in an ice bath and treated cautiously with 30 ml of 1M tetra-n-butylammonium fluoride in tetrahydrofuran. This mixture was refluxed for 1.5 hours and then concentrated to an oil. The oil was dissolved in 100 ml of ethyl acetate, washed with 50 ml each of 2N citric acid, 1M sodium bicarbonate and brine and dried. The solution was treated with activated carbon, filtered through a pad of hydrous magnesium silicate and concentrated to an oil. This oil was dissolved in 50 ml of 10% ethyl acetate in dichloromethane and chromatographed on two columns in the same solvent. Refractive index was monitored at S 20, 250 ml/minute. The main peak in hold-back volumes 6–10 was cut into 1 liter portions which were separately evaporated. The first three of these all crystallized and the solids were recrystallized form isopropyl ether and hexane, giving 0.7 g of (S)2-(t-butoxycarbonyl)amino-4-methyl-(S)1-(2-thiazolyl)pentan-1-ol as crystals, mp 121°–122° C.

From the mother liquors of the first three cuts and the latter cuts there was obtained 5.7 g of (S)2-(t-butoxycarbonyl)amino-4-methyl-(R)1-(2-thiazolyl)pentan-1-ol as an oil.

To 5.2 g of this oil was added 100 ml of anhydrous 2N hydrochloric acid in ethyl acetate with stirring. After stirring 1 hour the mixture was diluted with 100 ml of hexane, cooled in an ice-methanol bath at $-10°$ C. and the solid was collected, giving 4.34 g of (S)2-amino-4-methyl-(R)1-(2-thiazolyl)pentan-1-ol, hydrochloride as crystals, mp 134°–144° C.

To a solution of 3.5 g of this hydrochloride in 12 ml of water was added dropwise 1.8 ml of 15N ammonium hydroxide. Cooling and filtration gave 1.55 g of solid. Recrystallization from isopropanol gave the desired compound as crystals, mp 81°–82° C.; $[\alpha]_D^{26} = -12° \pm 1°$ (c, 1.0, methanol).

REFERENCE EXAMPLE 28 t-Butoxycarbonyl-L-cyclohexylalaninal

A 5.13 g portion of L-cyclohexylalanine was dissolved in a mixture of 60 ml of p-dioxane, 30 ml of water and 30 ml of 1N sodium hydroxide. To this solution, stirred and cooled in an ice bath, was added 7.19 g of di-t-butyldicarbonate. A suspension formed after a few minutes and the mixture was stirred at 0° C. for 1 hour, then concentrated in vacuo to about 40 ml. A 150 ml portion of ethyl acetate was added and the mixture was stirred and cooled in an ice bath while the pH was adjusted to 2 with potassium hydrogen sulfate. The aqueous layer was separated and extracted with two 75 ml portions of ethyl acetate. The organic layer and extracts were combined, washed with two 100 ml portions of brine, dried and evaporated in vacuo, giving 8.0 g of N$^\alpha$-t-butoxycarbonyl-L-cyclohexylalanine as a colorless gum; $[\alpha]_D^{26} = -2° \pm 1°$ (c, 1.0, chloroform).

To a solution of 9.52 g of imidazole in 80 ml of dichloromethane under argon, was added a solution of 6.22 g of phenyldichlorophosphate in 20 ml of dichloromethane. After stirring 1 hour, the mixture was cooled to 0° C. and a solution of 7.6 g of N$^\alpha$-t-butoxycarbonyl-L-cyclohexylalanine in 20 ml of dichloromethane was added over 10 minutes. This mixture was stirred for 1.5 hours at 0° to 5° C., then 3.28 g of N,O-dimethylhydroxylamine, hydrochloride was added. This mixture was stirred for 19 hours at 0° to 5° C., then diluted with 1000 ml of dichloromethane and washed with 100 ml of 1N hydrochloric acid, 80 ml of 0.5 N hydrochloric acid, two 80 ml portions 50% saturated potassium carbonate solution and 80 ml of brine. The organic layer was dried and evaporated, giving 8.38 g of N-methoxy-N-methyl-N$^\alpha$-t-butoxycarbonyl-L-cyclohexylalanine as a colorless gum $[\alpha]_D^{26} = -10° \pm 1°$ (c, 1.0, chloroform).

To a suspension of 1.25 g of lithium aluminum hydride in 100 ml of diethyl ether under argon, chilled to 0° C. was added a solution of 7.85 g of N-methoxy-N-methyl-N$^\alpha$-t-butoxycarbonyl-L-cyclohexylalaninamide in 20 ml of diethyl ether. This mixture was stirred at 0° C. for 0.5 hour, then a solution of 19 g of potassium hydrogen sulfate in 100 ml of water was added very slowly. When addition was complete, stirring was continued for 0.5 hour without cooling. The aqueous layer was separated and extracted with three 50 ml portions of diethyl ether. The organic layer and extracts were combined, washed with two 50 ml portions of 1N hydrochloric acid, 50 ml of saturated sodium bicarbonate, 50 ml of brine, dried and the solvent removed in vacuo, giving 6.5 g of the desired compound as a colorless gum; $[\alpha]_D^{26} = +12° \pm 1°$ (c, 1.135, chloroform).

REFERENCE EXAMPLE 29

(S)2-Amino-3-cyclohexyl-(R)1-(2-thiazolyl)propan-1-ol, and (S)2-Amino-3-cyclohexyl-(S)1-(2-thiazolyl)propan-1-ol To a solution of 6.35 g of 1,1-dimethylethyl-(S)-(2-cyclohexyl-1-formylethyl)carbamate in 15 ml of dichloromethane under argon, was added 5.89 g of 2-trimethylsilylthiazole with stirring and cooling in an ice-water bath. The solution was next stirred under argon at room temperature for 2.5 days, then cooled in an ice bath and 38 ml of 1M tetra-n-butylammonium fluoride in tetrahydrofuran was added. After 15 minutes at room temperature the volatiles were removed in vacuo. The residue was partitioned between 150 ml of ethyl acetate and 50 ml of water. The organic layer was separated, washed with two 50 ml portions of water and 50 ml of brine, dried and the solvent removed in vacuo, giving 8.19 g of light yellow gum. A 7.48 g portions of this gum was dissolved in a mixture of 20 ml of dichloromethane and 8.5 ml of trifluoroacetic acid and stirred for 2 days. The mixture was poured into 120 ml of 1N sodium hydroxide. The organic layer was separated and the aqueous layer extracted with two 75 ml portions of dichloromethane. The organic layer and extracts were combined, washed with 60 ml of brine, dried and the solvent removed in vacuo. The resulting 5.69 g of solid residue was flash chromatographed on 220 g of silica gel (230–600 mesh). Elution with 4% methanol in ethyl acetate gave, in the first major fraction, 2.63 g of (S)2-amino-3-cyclohexyl-(R)1-(2-thiazolyl)propan-1-ol as a white solid. $[\alpha]_D^{26} = -18° \pm 1°$ (c, 0.743 methanol).

Elution with 6% methanol in ethyl acetate gave 0.65 g (S)2-amino-3-cyclohexyl-(S)1-(2-thiazolyl)propan-1-ol as a colorless gum.

REFERENCE EXAMPLE 30

(S)2-(tert-Butoxycarbonyl)amino-3-phenyl-(R,S)-1-(2-thiazolyl)propan-1-ol

To a solution of 8.28 g of 2-bromothiazole in 100 ml of ether at $-78°$ C., under argon, was added 21.7 ml of n-butyl lithium in hexane. The mixture was stirred at $-78°$ C. for 45 minutes then 6.8 ml of trimethylsilyl chloride was added. This mixture was stirred at $-78°$ C. for 1 hour, warmed to $-30°$ C. over 1 hour, then 0° C. over ½ hour and kept at 0° C. for 1 hour. The reaction was quenched with 50 ml of 50% saturated sodium bicarbonate and then diluted with 50 ml of ether. The ether solution was washed with 50 ml of brine, dried, filtered and evaporated, giving 10.81 g of 2-trimethylsilylthiazole as an amber colored oil.

A solution of 10.55 g of phenyldichlorophosphate in 50 ml of dichloromethane was added dropwise to a solution of 17.0 g of imidazole in 150 ml of dichloromethane. The resulting suspension was stirred under argon for 20 minutes, then 13.27 g of $N^{60}$-tert.-butyloxycarbonyl-L-phenylalanine was added in small portions and stirring was continued for 1 hour. A 5.85 g portion of N,O-dimethylhydroxylamine hydrochloride was added, stirring continued for 21 hours, then the mixture was diluted with 100 ml of dichloromethane and washed with three 100 ml portions of 1N hydrochloric acid, 100 ml of water, two 100 ml portions of 50% saturated sodium bicarbonate solution and 100 ml of brine. The mixture was then dried and evaporated, giving 15.87 g of N-methoxy-N-methylN$^\alpha$-t-butoxycarbonyl-L-phenylalaninamide.

A suspension of 2.38 g of lithium aluminum hydride in 300 ml of ether at 0° C. under argon was prepared and stirred. To this was added slowly a solution of 15.5 g of N-methoxy-N-methylN$^\alpha$-t-butoxycarbonyl-L-phenylalaninamide in 80 ml of tetrahydrofuran. This mixture was stirred at 0° C. for 2 hours, then a solution of 37 g of potassium biphosphate in 200 ml of water was added slowly. When addition was complete the mixture was stirred at room temperature for 30 minutes. The organic phase was separated. The aqueous phase was extracted with two 200 ml portions of ether. The combined organic phase and extracts was washed with 200 ml portions of 1N hydrochloric acid, 200 ml of sodium bicarbonate solution and 200 ml of brine, dried and evaporated. The residue was washed with petroleum ether (30°-60°) giving 10.1 g of white solid. To a solution of 3.74 g of this solid in 20 ml of dichloromethane was added 5.5 g of 2-trimethylsilylthiazole. After stirring for 1.5 hours, another 1.57 g of 2-trimethylsilylthiazole was added and stirring was continued for 20.5 hours. A 20 ml solution of 1N tetrabutylammonium fluoride in tetrahydrofuran was added, the mixture was stirred 10 minutes and then the solvents were evaporated. The residue was taken up in 100 ml of ethyl acetate, washed with two 50 ml portions of water, then 50 ml of brine, dried and evaporated, giving 5.83 g of the desired compound as an amber colored gum.

REFERENCE EXAMPLE 31

(S)2-Amino-4-methyl-(S)1-(1-methyl-1H-1,2,4-triazol-5-yl)-pentan-1-ol and
(S)2-Amino-4-methyl-(R)1-(1-methyl-1H-1,2,4-triazol-5-yl)-pentan-1-ol To a suspension of 15.2 g of sodium hydride (60% in oil) (washed with hexane) in 100 ml of tetrahydrofuran under argon was added slowly at 0° to 10° C. a solution of 25 g of 1,2,4-triazol in 100 ml of methanol. To this solution was added dropwise 25 ml of methyl iodide over 0.5 hour. The mixture was stirred at 0° C. for 1 hour and then refluxed for 15 minutes. The solution was concentrated under reduced pressure until sodium iodide began to precipitate. The mixture was diluted with 100 ml each of ether and dichloromethane, filtered and the filtrate concentrated to dryness. The residual solid was triturated with dichloromethane (100 ml) and filtered. The filtrate was dried over molecular sieves (3A) and passed through a thin pad of hydrous magnesium silicate. The solvent was removed under vacuum and the residue sublimed to give 7.72 g of 1-methyl-1,2,4-triazole, mp 18°-20° C.

To a solution of 5.3 g of 1-methyl-1,2,4-triazole in 100 ml of tetrahydrofuran under nitrogen at −75° C. was added via syringe 25.6 ml of n-butyllithium. The solution was stirred 1.5 hour at −75° C. and then 6.9 g of N-tert-butoxycarbonyl-L-leucinal in 25 ml of tetrahydrofuran at −75° C. was added. The mixture was stirred ½ hour each at −75° C. and at −23° C. the mixture was treated with 10 ml of saturated ammonium chloride and concentrated. The residue in 100 ml of ethyl acetate was washed with 50 ml of each of water, 2N citric acid, 1M sodium bicarbonate and brine and dried. The solution was filtered and concentrated to give 8.41 g (88%) f a colorless oil which partly crystallized. Two recrystallization from iso-propyl acetate afforded 1.85 of (S)2-(tert-butoxycarbonyl)amino-4-methyl-(R)1-(1-methyl-1H-1,2,4-triazol-5-yl)pentan-1-ol, mp 144°-145° C. $[\alpha]_D^{26} -26\pm1°$(c, 1.1, MeOH).

The combined method liquor fraction (5.47 g) was chromatographed on silica gel with ethyl acetate-dichloromethane (2:3) as solvent on a Waters Prep 500 instrument. Fractions containing the less polar diastereomer were combined and crystallized form ether/hexane to give 0.67 g (7% yield) of (S)2-tert-butoxycarbonyl)amino-4-methyl-(S)1-(1-methyl-1H-1,2,4-triazol-5-yl)pentan-1-ol as crystals, mp 114°-116° C., $[\alpha]_D^{26} = -38°\pm1$ (c, 1.2, MeOH).

To a suspension of 2.34 g of (S)2-(tert-butoxycarbonyl)amino-4-methyl-(R)1-(1-methyl-1H-1,2,4-triazol-5-yl)pentan-1-ol in 3.5 ml of ethyl acetate was added 25 ml of anhydrous 2N hydrogen chloride in ethyl acetate. The solution was stirred 1 hour at room temperature and the solvent removed under vacuum. The residue was dissolved in 3 ml of water and 1 ml of concentrated ammonium hydroxide added. The mixture wax extracted with three 12 ml portions of dichloromethane. The extract was dried and the solvent removed under vacuum to give 1.75 g of (S)2-amino-4-methyl-(R)1-(1-methyl-1H-1,2,4-triazol-5-yl)pentan-1-ol as an oil.

REFERENCE EXAMPLE 32

(S)2-Amino-4-methyl-(R)1-(2-thienyl)pentan-1-ol

A 0.81 g of portion of (S)2-(tert-butoxycarbonyl)amino-4-methyl-(R,S)-1-(2-thienyl)pentan-1-ol (Reference Example 25) was dissolved in 5 ml of dichloromethane and 2.1 ml of trifluoroacetic acid added. This mixture was stirred for 3 hours and then poured, with stirring, into 15 ml of ice-cold 2N sodium hydroxide. This mixture was diluted with 25 ml of dichloromethane, the organic layer separated and the aqueous layer extracted with 20 ml of dichloromethane. The organic layer and extract were combined, washed with saturated sodium chloride solution, dried and the solvent removed in vacuo. The residue use chromatographed on a silica gel column, eluting with ethyl acetate:hexane (1:4), giving 0.72 g of white solid; $[\alpha]_D^{26} = -141°\pm2$ (c, 0.570, methanol) which was identified (NMR spectrum) as (4S-trans)-4-(2-methylpropyl)-5-(2-thienyl)-2-oxazolidinone.

A 0.23 g portion of the above oxazolidione was dissolved in 5 ml of ethanol and 5 ml of 1N sodium hydroxide added. This solution was refluxed for 16 hours and then concentrated in vacuo. The residue was extracted with two 10 ml of portions of dichloromethane. The extracts were combined, dried and the solvent removed in vacuo, giving 0.2 g of the desired compound; Rf 0.045 [silica gel plate-ethyl acetate:hexane (1:2)].

REFERENCE EXAMPLE 33

(S)2-Amino-3-cyclohexyl-(R)1-(2-thienyl)propan-1-ol

To a solution of 1.57 g of N-methoxy-N-methyl-N$^\alpha$-t-butoxycarbonyl-L-cyclohexylaninamide (See Reference Example 28) in 10 ml of diethyl ether cooled to −78° C. was added under argon, 2.1 ml of 2.35M n-butyllithium in hexane. After stirring for 1 hour the mixture was allowed to warm to 0° C. To this solution was added a solution of 2-lithiothiophene in ether (prepared from 0.64 g of thiophene in 5 m. of ether and 3.2 ml of 2.35M n-butyllithium in hexane, stirred at 0° C. for 1 hour). This mixture was stirred at 0° C. for 2 hours, then quenched with 15 ml of 1N hydrochloric acid and diluted with 25 ml of ether. The organic layer was separated, washed successively with 15 ml of 1N hydrochloric acid, 10 ml of water and 15 ml of saturated aqueous sodium bicarbonate, dried and filtered through a short pad of hydrous magnesium silicate. The filter pad was washed with ether and the filtrate and wash combined. The solvent was removed in vacuo, and the residue washed with hexane, giving 1.38 g of tan solid. This solid was chromatographed on 50 g of silica gel eluting with ethyl acetate:hexane (1:20), giving 1.2 g of solid. This solid was crystallized from hexane containing a trace of ether, giving (S)1,1-dimethylethyl[1-(cyclohexylmethyl)-2-oxo-2-thienylethyl]carbamate $[\alpha]_D^{26} = +24° \pm 1$ (c, 1.10, methanol).

A solution of 0.51 g of the above carbamate in 8 ml of dry tetrahydrofuran was cooled to −78° C. under argon and 3 ml of 1.0M K-Selectride in tetrahydrofuran was added dropwise. This mixture was stirred at −78° C. for 4 hours and then quenched with 5 ml of saturated aqueous ammoninum chloride solution. After warming to room temperature, the tetrahydrofuran was removed in vacuo. The aqueous residue was diluted with 5 ml of water and 20 ml of etyl acetate added. The organic layer was separated, washed successively with two 5 ml of saturated aqueous ammonium chloride, 5 ml of saturated aqueous sodium bicarbonate and 5 ml of saturated sodium chloride solution, dried and the solvent removed in vacuo, giving (S)2-tert-butoxycarbonylamino-3-cyclohexyl-(R)1-(2-thienyl)propan-1-ol as a gum.

This gum is stirred with trifluoroacetic acid in dichloromethane, as described in Reference Example 32, to give the desired product as a solid.

The following examples illustrate the preparation of compounds of our invention.

EXAMPLE 1

N-[(Phenylmethoxy)carbonyl]-L-phenylalanyl-N-[(S)-1-formyl-2-phenylethyl]-L-2-(2-methylpropoxy)-glycinamide A solution of 1.16 g of N-[(phenylmethoxy)carbonyl]-L-phenylalanyl-L-2-(2-methylpropoxy)glycyl-N-methoxy-N-methyl-L-phenylalaninamide in 20 ml of ether and sufficient tetrahydrofuran to provide solution was added drop-wise to a mixture of 0.1 g of lithium aluminum hydride in 20 ml of ether, with stirring under an argon atmosphere. When addition was complete, stirring as continued 4 hours longer, then the mixture was cooled and treated with a solution of 0.48 g of potassium bisulfate in 20 ml of water. More ether and water were added, the layers separated and the aqueous layer extracted three times with ether. The ether extracts and layer were combined, washed three times each with 3N hydrochloric acid, sodium bicarbonate solution and saturated sodium chloride solution, dried, filtered and evaporated, giving 0.53 g of the desired compound as a glass, $[\alpha]_D^{26} = -19° \pm 3°$ C. (C-0.32, methanol).

EXAMPLE 2

N-[(Phenylmethoxy)carbonyl]-L-phenylalanyl-N-[(S)-1-formyl-2-phenylethyl]-D-2-(2-methylpropoxy)-glycinamide A 1.2 g portion of N-[(phenylmethoxy)carbonyl]-L-phenylalanyl-D-2-(2-methylpropoxy)glycyl-N-methoxy-N-methyl-L-phenylalaninamide was treated with lithium aluminum hydride in tetrahydrofuran as described in Example 1, giving 0.76 g of the desired compound as a glass, which became an amorphous solid after trituration with hexane $[\alpha]_D^{26} = 0°$ C. (c, 0.3, methanol).

EXAMPLE 3

N-[(Phenylmethoxy)carbonyl]-L-phenylalanyl-N-[(S)-1-formyl-3-methylbutyl]-L-2-(2-methylpropoxy)-glycinamide A solution of 0.74 g of N-[(phenylmethoxy)carbonyl]-L-phenylalanyl-L-2-(2-methylpropoxy)glycyl-N-methoxy-N-methyl-L-leucinamide in 10 ml of ether and 10 ml of tetrahydrofuran was added dropwise to a stirred mixture of lithium aluminum hydride in 20 ml of ether under an argon atmosphere. When addition was complete, the mixture was stirred 4 hours longer, then cooled and treated with a solution of 0.31 g of potassium bisulfate in 15 ml of water. The aqueous layer was separated, extracted with ether and the ether extracts combined with the ether layer. The ether solution was washed three times each with 6N hydrochloric acid, saturated sodium bicarbonate solution and saturated sodium chloride solution, dried, filtered and evaporated. The resulting glass was triturated with hexane, giving 0.28 g of the desired compound as a white amorphous solid $[\alpha]_D^{26} = -23° \pm 7°$ C. (c, 0.13 methanol).

EXAMPLE 4

N-[(Phenylmethoxy)carbonyl]-L-phenylalanyl-N-[(S)-1-formyl-3-methylbutyl]-D-2-(2-methylpropoxy)-glycinamide A 1.16 g portion of N-[(phenylmethoxy)carbonyl-L-phenylalanyl-D-2-(2-methylpropoxy)glycyl-N-methoxy-N-methyl-L-leucinamide was reacted with lithium aluminum hydride in ether as described in Example 1, giving 0.75 g of the desired compound as an amorphous solid, $[\alpha]_D^{26} = 0°$ c, 0.1, methanol).

EXAMPLE 5

N-[(Phenylmethoxy)carbonyl]-L-phenylalanyl-N-[(S)-1-formyl-2-phenylethyl]-L-2-(2-methylpropoxy)-glycinamide To 1.2 g of N-[(phenylmethoxy)carbonyl]-L-phenylalanyl-L-2-(2-methylpropoxy)glycyl-N-methoxy-N-methyl-L-phenylalaninamide in 20 ml of ether, cooled to 0° C. under argon, was added 0.18 g of lithium aluminum hydride. After 20 minutes. 0.09 g of lithium aluminum hydride was added. After 15 minutes ethyl acetate was added and the mixture was worked up as described in Example 1. The resulting glass was crystallized from hexane containing a small amount of ethyl acetate, giving 0.47 g of the desired compound as a crystalline solid, mp 164°-168° C. A sample recrystallized from ethyl acetate/hexane gave crystals mp 172°-174° C.; $[\alpha]_D^{26} = -23° \pm 7°$ (c, 0.13, methanol).

EXAMPLE 6

N-[(Phenylmethoxy)carbonyl]-L-phenylalanyl-N-(S)-1-formyl-3-methylbutyl]-L-2-(1-methylethoxy)glycinamide A solution of 0.7 g of N-[(phenylmethoxy)carbonyl]-L-phenylalanyl-L-2-(1-methylethoxy)glycyl-N-methoxy-N-methyl-L-leucinamide in 10 ml of ether and 10 ml of tetrahydrofuran was added to a stirred mixture of 0.6 g of lithium aluminum hydride in 20 ml of ether under and argon atmosphere. This mixture was stirred 4 hours, then cooled and treated with a solution of 0.31 g of potassium bisulfate in 25 l of water. The layers were separated, the aqueous layer extracted once with ether and this extract combined with the ether layer. The ether solution was washed three times each with 3N hydrochloric acid, sodium bicarbonate solution and saturated sodium chloride solution, dried, filtered and evaporated. The residual glass was slurried several times in hexane and then thoroughly dried giving the desired compound as an amorphous solid $[\alpha]_D^{26} = -24° \pm 4°$ (c, 0.26, methanol).

EXAMPLE 7

N-[(Phenylmethoxy)carbonyl]-carbonyl]-L-phenylalanyl-N-[(S)-1-formyl-3-methylbutyl]-D-2-(phenylmethoxy)glycinamide An 8 g portion N-[(phenylmethoxy)carbonyl]-L-phenylalanyl-D,-2-(phenylmethoxy)glycyl-N-methoxy-N-methyl-L-leucinamide was dissolved in 50 ml of anhydrous ether. To 25 ml of this solution, under nitrogen, was added 0.38 g of lithium aluminum hydride. The mixture was stirred for 1 hour, then quenched in ethyl acetate, treated with 37 ml of 0.35M potassium bisulfate, filtered through diatomaceous earth and washed with ether. The combined ether solutions were then washed three times with 3N hydrochloric acid, twice with 1N sodium bicarbonate and once with sodium chloride solution. The ethereal solution was dried, filtered and evaporated. The solid was crystallized from ether, giving 0.9g of the desired compound, mp 109°-114° C; $[\alpha]_D^{26} = +0.5° \pm 1°$ (c, 1.05, methanol).

EXAMPLE 8

N-[(Phenylmethoxy)carbonyl]-L-phenylalanyl-N-[(S)-1-formyl-3-methylbutyl]-L-2-(phenylmethoxy)glycinamide To a suspension of 3.3 g of N-[(phenylmethoxy)carbonyl]-L-phenylalanyl-L-2-(phenylmethoxy)glycyl-N-methoxy-N-methyl-L-leucinamide in 50 ml of ether at 3° C. under nitrogen, was added 0.52 g of lithium aluminum hydride. The mixture was maintained at 0°-6° C. and after 20 minutes 0.26 g of lithium aluminum hydride was added. The mixture was maintained at 0° C. for 15 minutes, then ethyl acetate and dichloromethane were added, followed by three 20 ml portions of 3N hydrochloric acid. The organic layer was separated, washed with three 20 ml portions of 1N sodium bicarbonate and brine, dried, diluted with ethyl acetate and filtered through a short bed of 200-340 mesh silica gel. The silica gel was washed with ethyl acetate and the combined filtrate and wash concentrated to dryness in vacuo. The residue was crystallized from ethyl acetate/diisopropyl ether, giving 1.35 g of the desired compound as crystals, mp 134°-137° C.; $[\alpha]_D^{26} = -44° \pm 1°$ (c, 1.25, methanol).

EXAMPLE 9

N-[N-(tert-Butoxycarbonyl)-L-phenylalanyl-L-leucyl]-(S)2-amino-4-methyl-(R,S)-1-(2-furanyl)pentan-1-ol A 1 mmole sample of (S)2-tert-butoxycarbonylamino-4-methyl(R,S)1-(2-furanyl)pentan-1-ol is stirred with 5 equivalents of trifluoroacetilc acid for 16 hours. The mixture is poured into 6 ml of 1N sodium hydroxide and the mixture extracted with dichloromethane. The extract is dried and the solvent removed. The (S)2-amino-4-methyl-(R,S)-1-(2-furanyl)pentan-1-ol is used without purification and couple to tert-butoxycarbonyl-L-phenylalanyl-L-leucine as described previously.

The product is purified by column chromatographed an silica gel (ethyl acetate-hexane as solvent) to give a solid.

EXAMPLE 10

N,N-Diethyl
N-[N-(tert-butoxycarbonyl)-L-phenylalanyl-L-leucyl]-5-[(S)2-amino-(R,S)1-hydroxy-4-methylpentyl]2-thiophenecarboxamide A 1 mmole sample of N,N-diethyl-5-[(S)2-tert-butoxycarbonylamino-(R,S)-1-hydroxy-4-methylpentyl]-2-thiophenecarboxamide is stirred with 5 equivalents of trifluoroacetic acid for 24 hours. The mixture is poured into 6 ml of 1N sodium hydroxide and extracted with dichloromethane. The extract is dried and the solvent removed. The crude N,N-diethyl-5-[(S)2-amino(R,S)-1-hydroxy-4-methylpentyl]-2-thiophenecarboxamide is used without purification and is coupled with tert-butoxycarbonyl-L-phenylalanyl-L-leucine as described previously. The crude product is purified by chromatography on silica gel (ethyl acetate-hexane) to give a solid.

EXAMPLE 11

N-[N-(Benzyloxycarbonyl)-L-phenylalanyl-L-2-(2-methylpropoxy)glycl]-(S)2-amino-4-methyl(R)1-(1-methyl-1H-1,2,4-triazol-5-yl)pentan-1-ol and
N-[N-(Benzyloxycarbonyl-L-phenylalanyl-D-2-(2-methylpropoxy)glycyl]-(S)2-amino-4-methyl-(R)1-(1-methyl-1H-1,2,4-triazol-5-yl)pentan-1-ol To a stirred suspension of 2.34 g of N-(benzyloxycarbonyl)-L-phenylalanyl-(D, L-)-2-(2-methylpropoxy)glycine in 6 ml of dichloromethane was added 0.78 ml of triethylamine and 2.42 g of benzotriazol-1-yloxytris(-dimethylamino)phosphonium hexafluorophosphate. After 3 minutes, 1.04 g of (S)2-amino-4-methyl-(R)1-(1-methyl-1H-1,2,4-triazol-5-yl)-pentan-1-ol in 6 ml of dichloromethane was added. After stirring overnight, the solution was refluxed 30 minutes and concentrated. The residue, dissolved in 50 ml of ethyl acetate, was washed with 25 ml each of 1N hydrochloric acid, 1M sodium bicarbonate and brine. The organic layer was dried and concentrated to give 4 g of an oily mixture of diastereomers.

Preparative high pressure liquid chromatography on silica gel with 4:1 hexane-ethyl acetate gave a less polar fraction, 0.66 g mp 70°-74° C., $[\alpha]_D^{26} = -34° \pm 1°$ (c, 1.2 methanol) identified as N-[N-(benzyloxycarbonyl)-L-phenylalanyl-L-2-(2-methylpropoxy)glycyl]-(S)2- amino-4-methyl-(R)1-(1-methyl-1H-1,2,4-triazol-5-yl)-pentan-1-ol.

The more polar isomer, 0.7 g, mp 135°–139° C., [α]$_D^{26}$=−4°±2° (c, 1, methanol) was identified as N-[N-(benzyloxycarbonyl)-L-phenylalanyl-D-2-(2-methylpropoxy)glycyl]-(S)2-amino-4-methyl-(R1-(1-methyl-1H-1,2,4-triazol-5-yl)-pentan-1-ol.

EXAMPLE 12

N-[N-(Benzyloxycarbonyl)-L-phenylalanyl-L-2-(2-methylpropxy)glycyl]-(S)2-amino-3-phenyl-(R)1-(2-thiazolyl)propan-1-ol and N-[N-(Benzyloxycarbonyl)-L-phenylalanyl-D-2-(2-methylpropoxy)glycyl]-(S)2-amino-3-phenyl-(R)1-(2-thiazoly)propan-1-ol A solution of 0.51 g of N-benzyloxycarbonyl)-L-phenylalanyl-(D,L)-2-(2-methylpropoxy)glycine in 2 ml of dichloromethane was added to a prepared solution of 0.26 g of phenyldichloromethane and 0.40 g of imidazole in 4 ml of dichloromethane. To this solution was added 0.24 g of (S)2-amino-3-phenyl-(R)1-(2-thiazolyl)-propan-1-ol and the mixture stirred for 24 hours at room temperature. To the mixture was added 20 ml of 0.5N hydrochloric acid and 30 ml of ethyl acetate. The organic layer was separated and washed with 15 ml of 0.5N hydrochloric acid, 30 ml of saturated potassium carbonate and 15 ml of brine. The organic layer was dried and the solvent removed to give 1.04 g of solid. This solid was chromatographed by flash chromatography on silica gel (230–400 mesh) with ethyl acetate-hexane (1:1) as solvent to give 0.28 g of the L, L isomer (first fraction): [α]$_D^{26}$=−23°±1 (c,1.04, chloroform) and 0.10 g of the L, D isomer (second fraction); [α]$_D^{26}$=−43°±2 (c, 0.57, chloroform).

EXAMPLE 13

N-[N-(Benzyloxycarbonyl)-L-phenylalayl-L-(2-methylpropoxy)glycyl]-(S)2-amino-3-phenyl-(R)1-(2-thiazolyl)propan-1-ol To a stirred suspension of 0.18 g of N-[(phenylmethoxy)carbonyl]-L-phenylalanyl-N-[(S)-1-formyl-2-phenylethyl]-L-2-(2-methylpropoxy)glycinamide in 0.5 ml of dichloromethane was added 51 mg of 2-trimethylsilylthiazole in 0.5 ml of dichloromethane. After 3 hours the milky suspension was diluted with 2 ml of dichloromethane and stirred overnight. The mixture was refluxed 15 minutes and then cooled in an ice bath. Tetra-n-butylammonium fluoride (0.5 ml of 2.5M in tetrahydrofuran) was added and the solution refluxed 1.5 hours. The solution was concentrated and the residue in 5 ml of ethyl acetate was washed with 5 ml each of 2N citric acid, 1M sodium bicarbonate and brine. The solution was dried, filtered through a thin layer of hydrous magnesium silicate and concentrated to give 0.13 g of a gum. This gum was chromatographed on three 20×20×0.2 cm preparative silica gel plates with hexane-ethyl acetate (1:1) for development and ethyl acetate for elution. Evaporation of the elution solvent (ethyl acetate) gave 25 mg of the product as a gum which was identical to the L,L isomer of Example 12 (pmr spectrum). Comparison by thin layer chromatography on silica gel with ethyl acetate-hexane (1:1) showed identical RF's.

EXAMPLE 14

N-[N-(Benzyloxycarbonyl)-L-phenylalanyl-L-2-(cyclohexyloxy)glycyl]-(S)2-amino-4-methyl-(R)1-(2-thiazolyl)pentan-1-ol and N-[N-(Benzyloxycarbonyl)-L-phenylalanyl-D-2-(cyclohexyloxy)glycyl]-(S)2-amino-4-methyl-(R)1-(2-thiazolyl)pentan-1-ol To a suspension of 2.3 g of N-[N-(benzyloxycarbonyl)L-phenylalanyl]-(D,L)-2)-cyclohexyloxy)glycine in 6 ml of dichloromethane was added 0.71 ml of triethylamine. To this solution was added 2.25 g of benzotriazol-1-yloxytris(dimethylamino)phosphonium hexafluorophosphate followed 2 minutes later by the addition of 1 g of (S)2-amino-4-methyl-(R)1-(2-thiazolyl)-pentan-1-ol.

After stirring overnight, the solution was refluxed 1 hour and concentrated under vacuum. The residue was dissolved in 50 ml of ethyl acetate and washed successively with 1N hydrochloric acid, 1M sodium bicarbonate and brine. The colorless solution was dried, filtered through a thin pad of hydrous magnesium silicate and concentrated to an oil (4.55 g). The preceding oil in 30 ml of hexaneethyl acetate (1:1) was filtered and chromatographed, with solvent ethyl acetate-hexane (1:1), on two prep 500 silica gel columns in series at high pressure. Hold-back volumes 4–7 (fraction A) and 9–12 (fraction B) contained the products. The solutions were concentrated separately to give from fraction A, 1.1 g of N-[N-(benzyloxycarbonyl)-L-phenylalanyl-L-2-(cyclohexyloxy)glycyl]-(S)2-amino-4-methyl-(R)1-(2-thiazolyl)-pentan-1-ol as a glass; [α]$_D^{26}$=−54°±1° (c, 1.3, methanol); Rf 0.39 on silica gel plates with solvent ethyl acetate-hexane (1:1).

Concentration of fraction B gave 1.11 g of N-[N-(benzyloxycarbonyl)-L-phenylalanyl-D-2-(cyclohexyloxy)-glycyl]-(S)2-amino-4-methyl-(R)1-(2-thiazolyl)pentan-1-ol as a glass [α]$_D^{26}$=−3°±1° (c, 1.4, methanol); Rf 0.19 on silica gel plates with solvent ethyl acetate-hexane (1:1).

EXAMPLE 15

N-[N-(Benzyloxycarbonyl)-L-phenylalanyl-L-2-(1-methylethoxy)glycyl]-(S)2-amino-4-methyl-(R)1-(2-thiazolyl)pentan-1-ol and N-[N-(Benzyloxycarbonyl)-L-phenylalanyl-D-2-(1-methylethoxy)glycyl]-(S)2-amino-4-methyl-(R)1-(2-thiazolyl)pentan-1-ol To a suspension of 1.7 g of N-[N-(benzyloxycarbonyl)-L-phenylalanyl-(D,L)-2-(1-methylethoxy)glycine] in 4 ml of dichloromethane was added 0.56 ml of triethylamine. To the resulting solution was added 1.8 g of benzotriazol-1-yloxytris(dimethylamino)phosphonium hexafluorophosphate followed 2 minutes later by the addition of 0.8 g of (S)2-amino-4-methyl-(R)1-(2-thiazolyl)pentan-1-ol in 1 ml of dichloromethane. The reaction was stirred overnight, refluxed 30 minutes, and diluted with 50 ml of ethyl acetate. After washing with 10 ml each of 1N hydrochloric acid, 1M sodium bicarbonate and brine, this solution was dried and filtered with charcoal through a thin pad of hydrous magnesium silicate. The filtrate was concentrated under vacuum to give 2.5 g of a gum. High pressure liquid chromatography (two prep-500 silica gel columns) in hexane-ethyl acetate (1:1) gave two well-separated (refraction index detection) peaks. Concentration of hold-back volumes 6-9 (fraction A) gave 0.76 g of N-[N-(benzyloxycarbonyl)-L-phenylalanyl-L-2-(1-methylethoxy)-glycyl]-(S)2-amino-4-methyl-(R)1-(2-thiazolyl)-pentan-1-ol as a glassy foam; $[\alpha]_D^{26}=|56°\pm1°$ (c, 1.5, methanol) Rf 0.32 on silica gel plates with ethyl acetate-hexane (1:1) as solvent.

Concentration of hold-back volume 12–15 (fraction B) gave a solid which was crystallized from isopropyl acetate to give 0.83 g of N-[N-(benzyloxycarbonyl)-L-phenylalanyl-D-2-(1-methylethoxy)glycyl]-(S)2-amino-4-methyl-(R)1-(2-thiazolyl)pentan-1-ol as crystals, mp 163°–164° C.; $[\alpha]_D^{26}=-8°\pm2°$ (c, 0.5 methanol); Rf 0.20 on silica gel plates with ethyl acetate-hexane (1:1) as solvent.

EXAMPLE 16

N-[N-(tert-Butoxycarbonyl)-L-phenylalanyl-L-leucyl]-(S)2-amino-4-methyl-(R)1-(2-thienyl)-pentan-1-ol A mixture of 0.16 g of phenyldichlorophosphate and 0.26 g of imidazole in 2 ml of dichloromethane was stirred for 0.5 hour, then cooled to 0° C. and 0.28 g of N-(tert-butoxycarbonyl)-L-phenylalanyl-L-leucine in 2 ml of dichloromethane was added. This mixture was stirred at −15° C. for 1 hour. A 0.1 g portion of (S)2-amino-4-methyl-(R)1-(2-thienyl)pentan-1-ol was added, this mixture was stirred at −15° C. for 20 hours and then diluted with 10 ml of water and 20 ml of ethyl acetate. After warming to room temperature, the organic layer was separated, washed with two 10- ml portions of 0.5N hydrochloric acid, 10 ml of 1N sodium hydroxide and 10 ml of saturated sodium chloride solution, dried and the solvent removed in vacuo. The 0.31 g of residue was dissolved in 2 ml of methanol, 1 ml of 1N sodium hydroxide was added, this mixture stirred for 1 hour and then diluted with 2 ml of water. The methanol was removed and the aqueous suspension extracted with 15 ml of ethyl acetate. The extract was washed with saturated sodium chloride solution, dried and filtered through a thin pad of hydrous magnesium silicate. The pad was washed with ethyl acetate. The filtrate and wash were combined and concentrated in vacuo. The solid residue was washed with hexane, giving 0.27 g of the desired product as a white solid; Rf=0.72 [silica gel plate; ethyl acetate:hexane (1:1); $[\alpha]_D^{26}-34\pm2$ (c, 0.48, methanol).

EXAMPLE 17

N-[N-tert-Butoxycarbonyl)-L-phenylalanyl-L-leucyl]-(S)2-amino-3-cyclohexyl-(R)1-(2-furanyl)propan-1-ol

A. 1,1-Dimethylethyl (S)-[1-(cyclohexylmethyl)-2-(2-furanyl)-2-oxoethyl]carbamate A solution of 1.57 g of N-methoxy-N-methyl-N$^\alpha$-t-butoxycarbonyl-L-cyclohexylalaninamide in 15 ml of dry tetrahydrofuran was cooled to −78° C. under argon. To the solution was added dropwise 5.9 ml of secondary butyllithium (0.85M in hexane). The viscous mixture was stirred at −78° C. for 1.5 hour and then warmed to 0° C. and stirred for 5 minutes. (solution A)

A solution of 0.73 ml of furan in 5 ml of dry tetrahydrofuran was cooled to 0° C. and 3.8 ml of n-butyllithium (2.35M in hexane) added. The yellow suspension was stirred at 0° C. for 1.7 hour and then allowed to warm to room temperature for 15 minutes (yellow solution B).

The yellow solution B was added to solution A and the mixture stirred at 0° C. for 1.5 hours. The mixture was quenched with 5 ml of saturated aqueous ammonium chloride and the solvent tetrahydrofuran removed under vacuum. The residue was diluted with 50 ml of ethyl acetate and 20 ml of 1N hydrochloric acid. The organic phase was separated and washed successively with 10 ml of 1N hydrochloric acid, 20 ml of water, 20 ml of saturated sodium bicarbonate, 20 ml of brine and dried over sodium sulfate. The solvent was removed under vacuum to give 1.63 g of a light brown gum. This gum was dissolved in ether-hexane (1:5) and the solution filtered through a thin pad of hydrous magnesium silicate. The pad was washed with ether-hexane (1:5) and the filtrate concentrated. The residue was triturated with hexane to give 1.23 g of light yellow crystals; $[\alpha]_D^{26}+41°\pm1°$ (c, 1.14, methanol).

B. (S)2-(N-tert-Butoxycarbonyl)amino-3-cyclohexyl-(R,S)1-(2-furanyl)propan-1-ol A solution of 0.16 g of 1,1-dimethylethyl (S)-[1-(cyclohexylmethyl)-2-(2-furanyl)-2-oxoethyl]carbamate in 2 ml of dry tetrahydrofuran and 0.2 ml of methanol was cooled to 0° C. under argon and 23 mg of sodium borohydride added. The solution was stirred at 0° C. for 1 hour and quenched with 2 ml of saturated aqueous ammonium chloride. The organic solvent was removed under vacuum and the residue diluted with 5 ml of water and extracted with 10 ml of ethyl acetate. The organic layer was separated, washed successively with 5 ml of 0.5N hydrochloric acid, 5 ml of saturated sodium bicarbonate, 5 ml of brine and dried over sodium sulfate. The solvent was removed under vacuum to give 0.19 g of gummy solid.

C. (4S-trans) 4-(Cyclohexylmethyl)-5-(2-furanyl)-2-oxazolidione

To a solution of 0.23 g of (S)2-(N-tert-butoxycarbonyl)amino-3-cyclohexyl-(R,S)1-(2-furanyl)propan-1-ol in 3 ml of dichloromethane was added 0.06 ml of trifluoroacetic acid. The solution was stirred for 23 hours at room temperature, washed with 1N sodium hydroxide, dried over sodium sulfate and the solvent removed to give 0.17 g of solid.

D. (S)2-Amino-3-cyclohexyl-(R)1-(2-furanyl)propan-1-ol

A 0.15 g sample of (4S-trans) 4-(cyclohexylmethyl)-5-(2-furanyl)-2-oxazolidinone was dissolved in a mixture of 3 ml of ethanol and 3 ml of 1N sodium hydroxide. The solution was refluxed for 17 hours, diluted with 3 ml of water and concentrated under vacuum to remove the ethanol. The aqueous residue was extracted with two 5 ml portions of dichloromethane and the extracts dried over sodium sulfate. The solvent was removed to give 0.15 g of solid which was washed with hexane to give 0.13 g of white solid; $[\alpha]_D^{26}-10\pm2$ (c, 0.507, methanol).

E. A mixture of 0.12 g of phenyl dichlorophosphate and 0.12 g of imidazole in 2.5 ml of dichloromethane was stirred at room temperature for 1 hour and then cooled to −15° C. under argon. N-(tert-butoxycarbonyl)-L-phenylalanyl-L-leucine (0.21 g) was added in portions and the mixture stirred for 1 hour. To the above mixture was added 80 mg of (S)2-amino-3-cyclohexylmethyl-(R)1-(2-furanyl)propan-1-ol in 0.5 ml of dichloromethane. The mixture was stirred at −15° C. for 23 hours, and diluted with 15 ml of ethyl acetate and 10 ml of 0.5N hydrochloric acid. The organic layer was separated and washed successively with 5 ml of 0.5N hydrochloric, 5 ml of 1N sodium hydroxide, 5 ml of brine and dried over sodium sulfate. The solvent was removed under vacuum to give 0.24 g of solid. This solid was dissolved in 2 ml of methanol and 1 ml of 1N sodium hydroxide and the mixture stirred for 1 hour. The mixture was diluted with 4 ml of water and concentrated to remove the methanol. The residue was extracted with 10 ml of ethyl acetate and the extract dried over sodium sulfate. The extract was filtered through a thin pad of hydrous magnesium silicate and the pad washed with ethyl acetate. The filtrate was concentrated under vacuum to give 0.16 g of solid. Washing the solid with hexane gave 0.15 g of the product of the Example as a white solid: $[\alpha]_D^{26} -31 \pm 2$ (c, 0.58, methanol).

EXAMPLE 18

N-[(Phenylmethoxy)carbonyl]-L-phenylalanyl-L-2-(2-methylpropoxy)glycyl]-(1R,2S)-2-amino-3-cyclohexyl-1-(2-thiazolyl)propan-1-ol, and
N-[(Phenylmethoxy)carbonyl]-L-phenylalanyl-D 2-(2-methylpropoxy)glycyl-(1R,2S)-2-amino-3-cyclohexyl-1-(2-thiazolyl)propan-1-ol To a solution of 0.19 g of N,N-carbonyldiimidazole in 3 ml of dichloromethane under argon, was added 0.51 g of N-[(phenylmethoxy)carbonyl]-L-phenylalanyl-D,L-2-(2-methylpropoxy)glycine. The solution alanyl-D,L-2-(2-methylpropoxy)glycine. The solution was stirred for 1 hour and then 0.24 g of (S)2-amino-3-cyclohexyl-(R)1-(2-thiazolyl)propan-1-ol was added. After stirring for 1 day, a solution of 0.26 g of N-[(phenylmethoxy)carbonyl]-L-phenylalanyl-D,L-2-(2-methylpropoxy)glycine activated with 0.10 g of N,N-carbonyldiimidazole was added. After stirring 21 hours this addition was repeated. The solution was stirred overnight, then diluted with 40 ml of ethyl acetate and washed with 2×20 ml of 0.5N hydrochloric acid, 2×20 ml of 50% saturated potassium carbonate solution and 20 ml of brine. The organic layer was dried and evaporated in vacuo. The residue was chromatographed on silica gel, eluting with ethyl acetate:-hexane (2:3), giving 0.21 of N-[(phenylmethoxy)carbonyl]-L-phenylalanyl-L-2-(2-methylpropoxy)-(1R,2S)-2-amino-3-cyclohexyl-1-(2-thiazolyl)propan-1-ol as a white solid; $[\alpha]_D^{26} = -48° \pm 3°$ (c, 0.365, methanol) and 0.14 g of N-[(phenylmethoxy)carbonyl]-L-phenylalanyl-D-2-(2-methylpropoxy)glycyl-(1R,2S)-2-amino-3-cyclohexyl-1-(2-thiazolyl)propan-1-ol as a white solid; $[\alpha]_D^{26} = -19° \pm 3°$ (c, 0.366, methanol).

EXAMPLE 19

N-[N-[(Phenylmethoxy)carbonyl)-L-phenylalanyl-D,L-2-(isopropylthio)glycyl]-(S)2-Amino-3-cyclohexyl-(R)1-(2-thiazolyl)propan-1-ol To a solution of 4.1 g of N-(phenylmethoxy)carbonyl-3-L-phenylalanyl-D,L-2-hydroxyglycine in 50 ml of methanol (cooled in an ice bath) was added 0.3 ml of concentrated sulfuric acid. The mixture was chilled 16 hours at 0° C. to 5° C., filtered and the solid washed with ether to give 2.67 g of N-[N-(phenylmethoxy)carbonyl-L-phenylalanyl]-2-hydroxyglycine, methyl ester, as white crystals, in mp 117°-127° C.; $[\alpha]_D^{26} +4° \pm 2$ (C, 0.52, methanol).

A solution of 0.30 g of the preceding compound, 0.722 ml of isopropylmercaptan and 16 mg of 1-naphthylenesulfonic acid in 6 ml of dichloromethane was refluxed under argon over night. An additional 0.725 ml of isopropylmercaptan was added and the mixture refluxed 24 hours. The solvent was removed and the residue dissolved in chloroform. The solution was washed with 10% sodium carbonate (emulsion) (methanol added). The organic layer was separated and the aqueous layer extracted with chloroform. The combined organic layer and extracts was washed with saturated sodium chloride solution, dried (MgSO$_4$) and the solvent removed under vacuum. The residue (0.36 g) was chromatographed by flash chromatography on silica gel with chloroform as eluent to give 0.13 g of N-[(phenylmethoxy)carbonyl]-L-phenylalanyl-D,L-2-(isopropylthio)glycine, methyl ester as white crystals, mp 100°-103° C.

The preceding compound in methanol with 1 mole equivalent of 1N sodium hydroxide gives N-[(phenylmethoxy)carbonyl]-L-phenylalanyl-D,L-2-(isopropylthio)glycine as a glass.

The preceding compound was also prepared in the following manner. To a solution of 0.5 g of N-[(phenylmethoxy)carbonyl)] 3-L-phenylalanyl-D,L-2-hydroxyglycine and, 0.624 ml of isopropylmercaptan in 5 ml of acetic acid under argon was added 0.15 ml of sulfuric acid. The mixture was stirred at room temperature for 2 days (all solids dissolved) and poured onto ice-water. The mixture was extracted with ethyl acetate (several times). The combined extracts were washed with water. The organic layer was dried (MgSO4) and the solvent removed to give 0.48 g of N-[(phenylmethoxy)carbonyl]-L-phenylalanyl-D,L-2-(isopropylthio)glycine as a clear glass.

The preceding compound is activated with N,N-carbonyldiimidazole in dichloromethane and reacted with (S)2-amino-3-cyclohexyl-(R)1-(2-thiazolyl)propan-1-ol as described for Example 18 to give N-[(phenylmethoxy)carbonyl]-L-phenylalanyl-D,L-2-(isopropylthio)-glycyl]-(S)2-amino-3-cyclohexyl-(R)1-(2-thiazolyl)propan-1-ol as a glass.

EXAMPLE 20

N-[N-[(Phenylmethoxy)carbonyl]-L-phenylalanyl-D,L-2-(2-methylpropoxy)glycyl]-(1R,2S)-2-amino-4-methyl-1-(2-imidazolyl)pentan-1-ol A solution of 18.4 g of 1-[[2-(trimethylsilyl)methoxy]-methyl]-1H-imidazole in 80 ml of tetrahydrofuran under argon was chilled to −75° C. and to the solution was added 37.2 ml of n-butyllithium in hexane (2.5M). After stirring at −78° C. for 1 hour a solution of 10.0 g of N-t-butoxycarbonyl-L-leucinal in 20 ml of tetrahydrofuran was added. The mixture was stirred at −78° C. for 1.5 hour, the cooling bath removed for 5 minutes, and the mixture quenched with 30 ml of saturated ammonium chloride solution. The tetrahydrofuran was removed under vacuum and the aqueous residue diluted with 30 ml of water and then extracted with 300 ml of ethyl acetate. The organic layer was washed with saturated sodium bicarbonate (50 ml), saturated sodium chloride solution and dried (Na$_2$SO$_4$). The solvent was removed under vacuum to give 29.0 g of an amber oil. Chromatography on silica gel with ethyl acetate-hexane (2:3) gave 8.2 g of solid. This solid was chromatographed on silica gel with ethyl acetate-hexane (3.2) as eluant to give 4.14 of (S)2-(t-butoxycarbonyl)amino-4-methyl-(R)1-[2-[N-[2-(trimethylsilyl)ethoxy)methyl-]imidazolyl]pentan-1-ol as a white solid: $[\alpha]_D^{26} +8° \pm 2$ (C) 0.583, methanol). To 0.21 g of the preceding compound in 1 ml of dichloromethane was added 0.39 ml of trifluoroacetic acid and the solution stirred for 2 hours at room temperature under argon. The mixture was diluted with 10 ml of dichloromethane and poured into ice-cold 1N sodium hydroxide. The organic layer was separated and the aqueous layer extracted with dichloromethane. The organic layer and extracts were combined, dried (Na$_2$SO$_4$) and the solvent removed to give 0.15 g of (S)2-amino-4-methyl-(R)1-[2-[2-trimethylsilyl)ethoxy]methyl]imidazolyl]pentan-1-ol as a white solid.

As described for Example 18, N-[phenylmethoxy)carbonyl]-L-phenylalanyl-D,L-2-(2-methylpropoxy)glycine is activated with N,N-carbonyldiimidazole in 3 ml of dichloromethane and to this solution is added 0.15 g of (S)2-amino-4-methyl-(R)1-[1-[2-[N-[2-(trimethylsilyl)ethoxy]methyl]imidazolyl]pentan-1-ol. After stirring over night the mixture is diluted with ethyl acetate washed, successively, with 0.5N hydrochloric acid, 50% saturated potassium carbonate solution and saturated sodium chloride solution. The organic layer is dried, the solvent removed and the residue dissolved in tetrahydrofuran. To the solution is added 3 ml of tetra-n-butylammonium fluoride in tetrahydrofuran (1.0M), 0.4 ml of triethylamine and 0.4 ml of water. The mixture is refluxed for 24 hour and concentrated under vacuum. The aqueous residue is extracted with ethyl acetate, the extract dried and the solvent removed to give N-[phenylmethoxy)carbonyl]-L-phenylalanyl-D,L-2-(2-methylpropoxy)glycyl]-(1R,2S)-2-amino-4-methyl-1-(2-imidazolyl)pentan-1-ol as a white glass.

EXAMPLE 21

N-[N-[Phenylmethoxy)carbonyl]-L-phenylalanyl-D,L-2-ethoxyglycyl]-(S)2-amino-4-methyl-(R)1-(2-pyridinyl-pentan-1-ol To 2-bromopyridine (3.16 g) in 20 ml of dry tetrahydrofuran cooled to −78° C. under argon was added slowly 11.2 ml of n-butyl lithium in tetrahydrofuran (2M). The solution was stirred for 5 minutes and then 2.1 g of N-t-butoxycarbonyl-L-leucinal in 10 ml of tetrahydrofuran was added. The mixture was stirred for 35 minutes, then quenched with 10 ml of saturated sodium sulfate solution, warmed to room temperature and poured into 50 ml of water. The mixture was extracted with ethyl acetate. The extract was dried (Na$_2$SO4) and the solvent removed under vacuum. The residue was chromatographed over silica gel with ethyl acetateexane (3:7) as eluent and then ethyl acetate-hexane (1:1) as eluent to give 0.62 g of (S) 2-tert-butoxycarbonyl-amino-4-methyl(R,S)1-(2-pyridinyl)pentan-1-ol as a yellow oil; $[\alpha]_D^{26} -21°\pm3°$ (C, 0.329, dichloromethane). A 4.12 sample of the preceding compound in a mixture of 15 ml of dichloromethane and 5 ml of acetic anhydride was stirred at room temperature for 22 hours. The mixture was concentrated under vacuum. The residue was dissolved in dichloromethane and the solution washed with saturated agneous sodium carbonate, dried (Na$_2$SO$_4$) and the solvent removed. The residue was chromatographed over silica gel with 30% ethyl acetate in hexane to give 1.55 g of (S) 2-tert-butoxycarbonylamino-4-methyl-(S)1-(2-pyridinyl)pentan-1-ol, 0-acetate as crystals, mp 83°-84° C.; $[\alpha]_D^{26} -62°\pm1°$ (C. 1.01, dichloromethane) and (S) 2-tert-butoxycarbonylamino-4-methyl-(R)1-(2-pyridinyl)pentan-1-ol, 0-acetate as an amber oil; $[\alpha]_D^{26} +3°\pm1°$ (C, 1.-66, methanol).

A 3.32 g sample of (S) 2-tert-butoxycarbonyl-amino-4-methyl-(R)1-(2-pyridinyl)pentan-1-ol, 0-acetate was dissolved in a mixture of 3 ml of methanol and 8 ml of 5N sodium hydroxide. The solution was stirred at 10° C. for 2 hours and then extracted with dichloromethane. The extract was dried (Na$_2$SO$_4$) and the solvent removed under vacuum to give 2.69 g of (S) 2-tert-butoxycarbonylamino-4-methyl-(R)1-(2-pyridinyl)-pentan-1-ol as an oil. To the preceding compound (2.69 g) was added 15 ml of 2N anhydrous hydrochloric acid in ethyl acetate. After stirring at room temperature, the solvent was removed under vacuum to give 2.46 g of (S) 2-amino-4-methyl-(R)1-(2-pyridinyl)-pentan-1-ol, dihydrochloride as tan crystals, mp 152°–154° C. To a solution of N-[(phenylmethoxy)carbonyl]-L-phenylalanyl-D,L-2-ethoxyglycine (2.0 g; 5 mmol) (Reference Example 12) and 5 mmol of 2-ethoxy-1(2H)-quinolinecarboxylic acid ethy! ester in 50 ml of dichloromethane is added 5 mmol of (S)-2-amino-4-methyl-(R)1-(2-pyridinyl)pentan-1-ol, dihydrochlorde and 4 ml of triethylamine in 25 ml of dichloromethane. The mixture is stirred at room temperature for 20 hours and worked-up as described for Reference Example 8 to give N-[N-[(phenylmethoxy)carbonyl]-L-phenylalanyl-D,L-2-ethoxyglycyl]-(S)2-amino-4-methyl-(R)1-(2-pyridinyl pentan-1-ol as a solid.

EXAMPLE 22

N-[N-(Phenylmethoxy)carbonyl]-L-phenylalanyl-D,L-2-(2-methylpropoxy)glycyl]-(S)2-amino-3-cyclohexyl-(R)1-(2-pyridinyl)propan-1-ol To a solution of 3.16 g of 2-bromopyridine in 20 ml of dry tetrahydrofuran cooled to −78° C. under argon was added 11.6 ml of n-butyllithium in tetrahydrofuran (2.0M). After stirring for 5 minutes, 3.14 g of N-methoxy-N-methyl N$^{60}$-t-butoxycarbonyl-L-cyclohexylalaninamide in 20 ml of dry tetrahydrofuran was added. The dark solution was stirred for 1 hr at −78° C. and then quenched with 20 ml of saturated sodium sulfate solution. The mixture was allowed o warm to room temperature and was poured into 50 ml of water. The mixture was extracted with ethyl acetate and the extract dried (Na$_2$SO4). The solvent was removed under vacuum and the residue chromatographed on a silica gel column with ethyl acetate-hexane (1:1) as solvent to give 2.01 g of 1,1-dimethylethyl (S) [1-(cyclohexylmethyl-2-oxo-2-(2-pyridinyl)ethyl]-carbonate as an oil; $[\alpha]_D^{26} +35°\pm$ (C, 0.812, methanol). A solution of 1.35 g of the preceding compound in 30 ml of dry tetrahydrofuran under argon was chilled to −78° C. and 7.5 ml of lithium tri-sec-butyl borohydride in tetrahydrofuran (1.0M) was added. The mixture was stirred for 5 hours at −78° C. and 12 hours at room temperature. The cooled mixture (ice bath) was quenched with water (8 ml) and then 8 ml of 30% hydrogen peroxide was added dropwise. The mixture was extracted with ethyl acetate, the extract dried (Na$_2$SO4) and the solvent removed under vacuum. The residue was chromtographed on a silica gel column with ethyl acetate-hexane (2:3) as solvent to give 0.27 g of (S) 2-tert-butoxycarbonylamino-3-cyclohexyl-(R)1-(2-pyridinyl)propan-1-ol as a white solid.

A 3.12 g sample was recystallized from hexane to give 1.52 g of white crystals, m.p. 68°–69°C.: $[\alpha]_D^{26} +9°\pm1$ (C, 1.07, methanol).

To 2.36 g of the preceding compound was added 32 ml of 2N hydrochloric acid in ethyl acetate. After stirring overnight, 10 ml of 6N hydrochloric acid was added. The solution was stirred at room temperature for 3 hours, concentrated, made basic with concentrated ammonium hydroxide, and extracted with dichloromethane. The extract was dried over potassium carbonate and the solvent removed to give 1.39 g of an oil. The oil was crystallized from diisopropyl ether to give crystals which were sublimed under reduced pressure to give (S)2-amino-3-cyclohexyl-(R)1-(2-pyridinyl)propan-1-ol as white crystals, mp 57°-59° C.: $[\alpha]_D^{26} + 6° \pm 1°$ (C, 1.045, methanol).

To a solution of 1.0 g of N-[(phenylmethoxy) carbonyl]-L-phenylalanyl-D,L-2-(2-methylpropoxy)glycine (Reference Example 4) and 0.58 g of (EEDQ) 2-ethoxy 1(2H)-quinolinecarboxylic acid, ethyl ester in 25 ml of dichloromethane is added 2.33 mmole of (S) 2-amino-3-cyclohexyl-(R)1-(2-pyridinyl)propan-1-ol in 15 ml of dichloromethane. The mixture is stirred 15 hours and the solvent removed. The residue is worked-up as described for Reference Example 8 to give the product as a solid.

EXAMPLE 23

N-[N-[Phenylmethoxy)carbonyl]-L-phenylalanyl-D,L-2-(2-methylpropoxy)glycyl]-(S)2-Amino-3-cyclohexyl-(R)1-(2-thienyl)propan-1-ol Activation of N-[(phenylmethoxy)carbonyl]-L-phenylalanyl-D,L-2-(2-methylpropoxy)glycine with N,N-carbonyldiimidazole as described in Example 18 and reaction with (S)2-amino-3-cyclohexyl-(R)1-(2-thienyl)propan-2-ol in place of (S)2-amino-3-cyclohexyl-(R)1-(2-thiazolyl)propan-1-ol of Example 18 gives the product of the Example as a solid.

EXAMPLE 24

N-[N-]Phenylmethoxy)carbonyl]-L-phenylalanyl-D,L-2-(2-methylpropoxy)glycyl[-(S)2-amino 3-cyclohexyl-(R)1-(2-furanyl)propan-1-ol Activation of N-[(phenylmethoxy)carbonyl]-L-phenyalanyl-D,L-2-(2-methylpropxy)glycine with N,N-carbonyldiimidazole as described in Example 18 and reaction with (S)2-amino-3-cyclohexyl-(R)1-(2-furanyl)propan-1-ol in place of (S) 2-amino-3-cyclohexyl-(R)1-(2-thiazolyl)propan-1-ol of Example 18 gives the product of the Example as a solid.

EXAMPLE 25

N-[N-[(phenylmethoxy)carbonyl]-L-phenylalanyl-D,L-2-(isopropylthios)glycyl]-(S)2-amino-3-cyclohexyl-(R)1-(2-thienyl)propan-1-ol Activation of N-[(phenylmethoxy)carbonyl]-L-phenylalanyl-D,L-2-(isopropylthio)glycine with N,N-carbonyldiimidazole and reaction with (S)2-amino-3-cyclohexyl-(R)1-(2-thienyl)propan-1-ol in a manner described for Example 18 gives the product of the Example as a solid.

EXAMPLE 26

N-[N-[(Phenylmethoxy)carbonyl]-L-phenylalanyl D,L-2-(isopropylthio)glycyl]-(S)2-amino-3-cyclohexyl-(R)1-(2-furanyl)propan-1-ol Activation of N-[(phenylmethoxy)carbonyl]-L-phenylalanyl-D,L-2-(isopropylthio)glycine with N,N-carbonyldiimidazole and reaction with (S)2-amino-3-cyclohexyl-(R)1-(2-furnayl) propan-1-ol in a manner described for Example 18 gives the product of the Example as a solid.

EXAMPLE 27

N-[N-[(Phenylmethoxy)carbonyl]-L,L-2-(isopropylthio)glycyl]-(S)2-amino-4-methyl-(R)-1-(2-thiazolyl(pentan-1-ol To a solution of 0.15 g of N-[(phenylmethoxy)carbonyl]-L-phenylalanyl-D,L-2-(isopropylthio)glycine in 5 ml of dichloromethane under argon was added 86.3 mg. of 2-ethoxy-1(2H)-quinolinecarboxylic acid ethyl ester (EEDQ). After stirring 15 minutes a solution of (S) 2-amino-4-methyl-(R)1-(2-thiazolyl)pentan-1-ol in 2 ml of dichloromethane was added. The solution was stirred overnight at room temperature and then washed with 3N-hydrochloric acid, 10% sodium bicarbonate brine and dried (magnesium sulfate). The solvent was removed under vacuum to give 0.180 g of a clear foam. thin layer chromatography on silica gel plates with ethyl acetate-hexane (1:1) separated the two diastereomers N-[N[(phenylmethoxy)carbonyl]-L-phenylalanyl-D-2-(isopropylthio)glycyl]-(S)2-amino-4-methyl-(R)1-(2-thiazolyl)pentan-1-ol as crystals, mp 163°-164° C. and N-[N-[(phenylmethoxy)carbonyl]-L-phenylalanyl-L-2-(isopropylthio)glycyl]-(S)2-amino-4-methyl-(R)1-(2-thiazolyl)pentan-1-ol as a clear foam.

EXAMPLE 28

N-[N-[(Phenylmethoxy)carbonyl]-L-phenylalanyl-D, L-2-(2-N,N-dimethylaminoethylthio)glycol]-(S)2-amino-4-methyl-(R)1-(2-thiazolyl)pentan-1-ol A mixture of 0.5 g of N[(phenylthoxy)carbonyl]-L-phenylalanyl-D,L-2-hydroxyglycine and 0.212 g of 2-dimethylaminoethanethiol, hydrochloride in 6 ml of dry acetic acid under argon was stirred (slowly). To the mixture was added 1 ml of acetic acid saturated with dry gaseous hydrochloric acid. The thick mixture was stirred at room temperature for 20 hours (after 3 hours, solids had dissolved). The mixture was concentrated under vacuum. To the residue was added dry acetic acid and the mixture concentrated under vacuum. Toluene and ethanol were added to the residue and then the solvent was removed. Ethanol was added and then removed and the residue pumped under vacuum for 3 days to give 0.75 g of N-[(phenylmethoxy)carbonyl]-L-phenylalanyl-D,L-2-(2-N,N-dimethylaminoethylthio)glycine, hydrochloride, as a viscous oil. A 1.38 g sample of the preceding compound was purified by chromatography on a silica gel column with chloroform as eluent and then methanol-chloroform (1:4) as eluent. Fractions containing product were combined and the solvent removed to give 0.57 g of white solid.

A 0.47 g sample of the preceding compound was dissolved in 25 ml of N,N-dimethylformamide under argon. To the solution was added 0.154 g of N,N-carbonyldiimidazole and after stirring for 2 hours 0.19 of (S)2-amino-4-methyl-(R)1-(2-thiazolyl)pentan-1-ol was added. The mixture was stirred overnight and the solvents removed under high vacuum. The residue was dissolved in chloroform and the solution washed with saturated sodium bicarbonate (emulsion-water added and mixture filtered to break emulsion), and then washed with brine (emulsion). The organic layer was separated, dried over magnesium sulfate and the solvent removed to give 0.65 g of the product of the example as a tan oil.

EXAMPLE 29

N-[N-[(phenylmethoxy)carbonyl]-L-phenylalanyl-L-2-
C-1-methylethoxy)glycyl]-(S)2-amino-3-cyclohexyl-
(R)1-(2-pyridinyl)propan-1-ol and N-[N-[(Phenylmethoxy)carbonyl]-L-phenylalanyl-D-2-
(1-methylethoxy)glycyl]-(S)2-amino-3-cyclohexyl-
(R)1-(2-pyridinyl)propan-1-ol To a slurry of 0.30 g of N-[N-[(Phenylmethoxy)carbonyl]-L-phenylalanyl-D,L-2-(1-methylethoxy)glycine in 10 ml of dichloromethane was added 0.179 g of 2-ethoxy-1(2H)-quinolinecarboxylic acid, ethyl ester (EEDQ). After stirring 30 minutes the solid dissolved and 0.169 g of (S)2-amino-3-cyclohexyl-(R)1-(2-pyridinyl)propan-1-ol in 2 ml of dichloromethane was added. The solution was stirred 16 hours and was then washed with 10% sodium bicarbonate, brine and dried over magnesium sulfate. The solvent was removed to give 0.52 g of a tan foam. A 1.02 g sample of the preceding foam was chromatographed on a silica gel with ethyl acetate-dichloromethane (4:6) as solvent on a Watera Prop 500 instrument. Fractions containing the less polar diastereomer were combined to give 0.18 g of white foam. Fraction containing the more poler diastereomer were combined to give 0.17 g of white

EXAMPLE 30

N-[N-[(Phenylmethoxy)carbonyl]-L-phenylalanyl-L-2-
(isopropylthio)glycyl]-(S)2-amino-3-cyclohexyl-(R)1-
(2-pyridinyl)propan-1-ol To a solution of N-](phenylmethoxy)carbonyl]-L-phenylalanyl-D,L-2-(isopropylthio)glycine in 15 ml of dry tetrahydrofuran under argon was added 0.219 g of N,N-carbonyldiimidazole and the mixture stirred at room temperature for 2.5 hours. To this solution was added 0.254 g of (S)2-amino-3-cyclohexyl(R)1-(2-pyridinyl)propan-1-ol and the mixture was stirred at room temperature overnight. The solvent was removed and the residue dissolved in dichloromethane and the solution washed with 10% sodium bicarbonate and brine. The aqueous layer was extracted with dichloromethane and the organic layer and extracts combined, dried (Na$_2$SO$_4$) and the solvent removed. The residue (0.83 g) was chromatographed on silica gel with 45% ethyl acetate in dichloromethane as solvent. Fractions containing the fast moving component were combined to fine 0.26 g of the product of the example as a solid foam: $[\alpha]_D^{26}=18\pm1$ (C, 0.858°, CH$_3$OH) and 0.19 g of N-N[(phenylmethoxy)carbonyl]-L-phenylalanyl-D-2-(isopropylthio)glycyl]-(S)2-amino-3-cyclohexyl-(R)1-(2-pyridinyl)-propan-1-ol as a solid yellow foam: $[\alpha]_D^{26}-8°\pm$ (C, 1.205, CH$_3$OH).

EXAMPLE 31

N-[N-[(Phenylmethoxy)carbonyl]-L-phenylalanyl-L-2-
(1-methylethoxy)glycyl]-(S)2-amino-
3-cyclohexyl-(R)1-(2-thiazolyl)propan-1-ol To a solution of N,N-carbonyldiimidazole (0.12 g) in 3 ml of dichloromethane under argon was added a solution of N-[(phenylmethoxy)carbonyl-L-phenylalanyl-D,L-2-(1-methylethoxy)glycine (0.31 g) in 1 ml of tetrahydrofuran and the mixture stirred 1 hour. To this solution was added 0.18 g of (S)2-amino-3-cyclo hexyl-(R)1-2-thiazolyl)-1-(tert-butyldimethylsilyloxy)propane in 1 ml of tetrahydrofuran. The mixture was stirred at room temperature for 2 hours, diluted with 3 ml of water and the solvent removed. The residue was diluted with 20 ml of ethylacetate and 5 ml of 1N-hydrochloric acid. The organic layer was separated, washed with 10 ml of 0.5N hydrochloric acid, 10 ml of saturated sodium bicarbonate, brine and dried (Na$_2$SO$_4$). The solution was diluted with 10 ml of hexane and filtered through a thin pad of hydrous magnesium silicate. The pad was washed with 10 ml of ethylacetate-hexane (1:1) and the filtrate concentrated to dryness to give 0.4 g of a foamy solid. This solid (0.22 g) in 1 ml of tetrahydrofuran and 0.35 ml of tetra(n-butyl)ammonium fluoride (1.0M in tetrahydrofuran) was stirred at room temperature for 1 hour, diluted with 2 ml of water and the solvent removed. The residue was extracted with 10 ml of ethyl acetate and the extract washed with 3 ml of 0.5N hydrochloric acid, 3 ml of saturated sodium bicarbonate, brine and dried (Na$_2$SO$_4$). The solvent was removed and the residue chromatographed on silica gel by gradient elution with ethylacetate-hexane (2:3) to ethylacetatheexane (1:1). Fractions containing the faster moving component were combined and the solvent removed to give 0.10 g of the product of the example as a white solid $[\alpha]_D^{26}-37°\pm1$(C, 0.660, CHCl$_3$. Fraction containing the slower moving component gave 0.10 g of N-[N-[(phenylmethoxy)carbonyl-L-phenylalanyl-D-2-(1-methylethoxy)glycyl](S)2-amino-3-cyclohexyl-(R)1-(2-thiazolyl)propan-1-ol as a white solid: $[\alpha]_D^{26}+6°\pm2$ (C, 0.639, CHCl$_3$).

EXAMPLE 32

N-[N-[(Phenylmethoxy)carbonyl-L-phenylalanyl-L-2-
(isopropylthio)glycyl]-(S)2-amino-4-methyl-(R)1-(2-
thiazaolyl)pentan-1-ol A mixture of 0.5 g of N-[(phenylmethoxy)carbonyl]-L-phenylalanyl-L-2-hydroxyglycine, 0.624 ml of 2-propanethiol, 0.150 ml of concentrated sulfuric acid in 5 ml of glacial acetic acid was stirred under argon at room temperature for 3 days. The mixture was poured into ice-water and extracted with ethyl acetate. The combined extracts were washed with water and the solvent removed. The residue was dissolved in ethyl acetate, dried (MgSO$_4$) and the solvent removed. The residue was dried under high vacuum over solid potassium hydroxide to give a viscous oil. The oil was dissolved in ethyl acetate and the solvent removed (repeated several times). Drying under high vacuum gave 0.46 g of N-[(phenylmethoxy)carbonyl]-L-phenylalanyl-D,L-2-(isopropylthio)glycine as a foam: Mass spectrum (FAB); calc. (N+H), 431: Found (M+H), 431.

To the preceding compound (0.150 g) in 5 ml of dichloromethane under argon was added 86.3 mg. of N-ethoxycarbonyl-2-ethoxy-1,2-dihydroquinoline (EEDQ). After stirring 15 minutes, 69.8 mg of (S)2-amino-2-methyl(R)1-(2-thiazolyl)pentan-1-ol in 1.3 ml of dichloromethane was added and the mixture was stirred over night at room temperature. The mixture was washed with 3N hydrochloric acid, 10% sodium bicarbonate, brine and dried (MgSO$_4$). The solvent was removed to give 0.180 g of a foam. Chromatography on silica gel of a 0.49 sample with ethylacetate-dichloromethane (2:3) separated the two diastereomers. Fractions containing the faster moving compound were combined and the solvent removed. Drying under vacuum gave 0.160 g of the product of example as a clear foam: $[\alpha]_D^{26}-5°\pm1$ (C, 1.097, CH$_3$OH), and 0.10 g of N-[N-[(phenylmethoxy)carbonyl]-L-phenylalanyl-D-2-(isopropylthio)glycyl]-(S)2-amino-4-methyl-(R)1-(2- thiazolyl)pentan-1-ol as a white solid: [α]$_D^{26}$ −34°±1 (C, 1.00, CH$_3$OH).

EXAMPLE 33

N-[N-[(Phenylmethoxy)carbonyl]-L-phenylalanyl-L-2-(1-methylethoxy)glycyl]-(S)2-amino-3-cyclohexyl-(R)1-(2-pyridinyl)propan-1-ol A mixture of 0.30 g of N-[(phenylmethoxy)carbonyl-L-phenylalanyl-D,L-2-(1-methylethoxy)glycine, 0.179 g of N-ethoxycarbonyl-2-ethoxy-1,2-dihydroquinoline (EEDQ) in 10 ml of dichloromethane was stirred for 30 minutes. To the solution was added 0.169 g of (S)2-amino-3-cyclohexyl-(R)1-(2-pyridinyl)propan-1-ol in 2 ml of dichloromethane and the mixture stirred overnight. The solution was washed with 10% sodium bicarbonate, brine, dried (MgSO$_4$) and the solvent removed to give 0.520 g of solid. A 1.40 g sample was chromatographed on silica gel on a Water-Prep 50° HPLC apparatus with solvent ethylacetate-dichloromethane (2:3) as eluent to give 0.10 g of the produce of the example as a white amorphous solid: [α]$_D^{26}$ −27°±1 (C, 1.058, CH$_3$OH) and 0.093 g of N-[N-[(phenylmethoxy)carbonyl)-L-phenylalanyl-D-2-(1-methylethoxy)glycyl]-(S)2-amino-3-cyclohexyl-(R)1-(2-pyridinyl)propan-1-ol as a white solid: [α]$_D^{26}$ +20±1 (C, 1.05, CH$_3$OH).

We claim:

1. A compound of the formula:

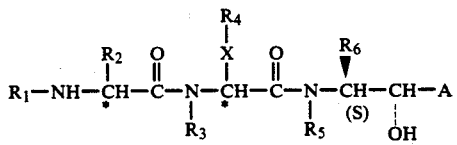

wherein R$_1$ is

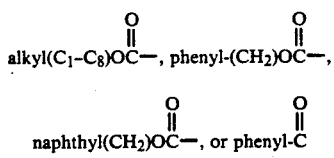

where n is an integer 1–4; R$_2$ is phenylmethyl, (2-thienyl)—CH$_2$—, (3-indolyl)CH$_2$—, or —CH$_2$-naphthyl; R$_3$ is hydrogen or methyl; R$_4$ is alkyl(C$_1$–C$_8$), (4-imidazolyl)CH$_2$—, or —CH$_2$CH$_2$N—[alkyl(C$_1$–C$_3$)]$_2$; R$_5$ is hydrogen or methyl; R$_6$ is alkyl(C$_1$–C$_6$), phenylmethyl, cyclohexylmethyl, X is —O— or —S—; and where A is

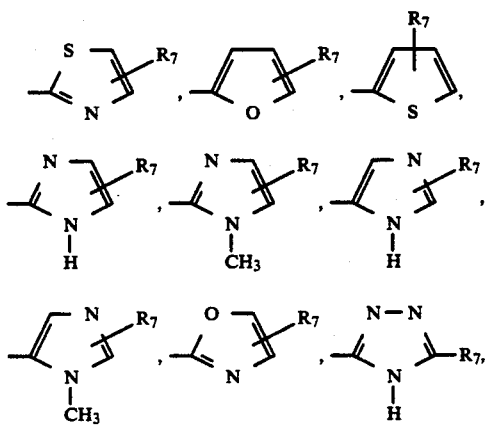

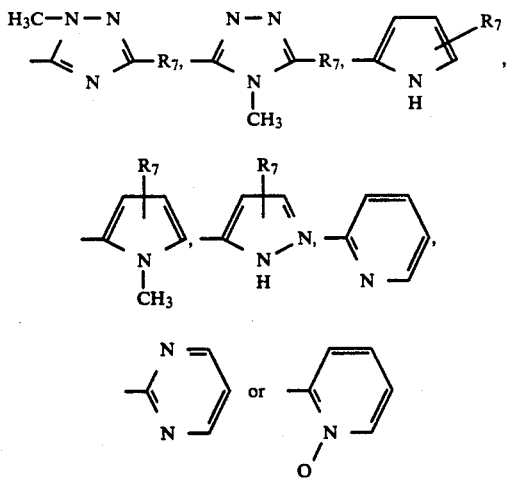

with the proviso that when A is

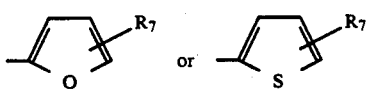

then x in formulae may also be a single bond; R$_7$ is hydrogen, alkyl(C$_1$–C$_3$) and COR$_8$; R$_8$ is NH$_2$, OH, —O—alkyl(C$_1$–C$_4$), —NH—alkyl(C$_1$–C$_4$), —N[alkyl(-C$_1$–C$_3$)]$_2$ and the asterisks denote asymmetric carbon atoms.

2. A compound according to claim 1 wherein the α-amino acids have the natural L configuration.

3. A compound according to claim 1 wherein the dipeptide or tripeptide unit has the L, L or the L, L, L configuration.

4. The compound according to claim 1, N-[N-(tert-butoxycarbonyl)-L-phenylalanyl-L-leucyl]-(S)2-amino-3-cyclohexyl-(R)1-(2-furanyl)propan-1-ol.

5. The compound according to claim 1 N-[N-(tert-butoxycarbonyl)L-phenylalanyl-L-leucyl]-(S)-2-amino-3-cyclohexyl-(R)1-(2-thienyl)propan-1-ol.

6. The compound according to claim 1 N-[N-(tert-butoxycarbonyl)-L-phenylalanyl-L-histidyl]-(S)2-amino-3-cyclohexyl-(R)-1-(2-thienyl)propan-1-ol.

7. The compound according to claim 1 N-[N-[(phenylmethoxy)carbonyl]-L-phenylalanyl-L-2-(2-methylpropoxy)glycyl]-(S)2-amino 3-cyclohexyl-(R)1-(2-imidazolylpropan-1-ol.

8. The compound according to claim 1 N-[N-[(phenylmethoxy)carbonyl]-L-phenylanalyl-L-2-(2-methylpropoxy)glycyl]-(S)2-amino-3-cyclohexyl-(R)1-(2-pyridinyl)propan-1-ol.

9. A compound according to claim 1 N-[N-[(phenylmethoxy)carbonyl]-phenylalanyl-L-2-(1-methylethoxy)glycyl]-(S)2-amino-3-cyclohexyl-(R)1-(2-thiazolyl)-propan-1-ol.

10. A compound according to claim 1 N-[N-[(phenylmethoxy)carbonyl]-L-phenylalanyl-L-1-(1-methylethoxy)glycyl]-(S)2-amino-3-cyclohexyl-(R)1-(2-pyridinylpropan-1-ol.

11. A compound according to claim 1 N-[N-[(phenylmethoxy)carbonyl]-L-phenylalanyl-L-2-(isopropylthio)glycyl]-(S)2-amino-3-cyclohexyl-(R)1-(2-thiazolyl)-propan-1-ol.

12. A compound according to claim 1 N-[N-[(phenylmethoxy)carbonyl]-L-phenylalanyl-L-2-(isopropylthio)glycyl]-(S)2 amino-3-cyclohexyl-(R)1-(2--pyridinyl)propan-1-ol.

13. A compound according to claim 1 N-[N-[(phenylmethoxy)carbonyl]-L-phenylalanyl-L-2-(2-methyl propoxy)glycyl]-(S)2-amino-3-cyclohexyl-(R)1-(2-thiazolyl)propan-1-ol.

14. A compound according to claim 1 N-[N-[(phenylmethoxy)carbonyl]-L-phenylalanyl-L-2-(ethoxy)-glycyl]-(S)2-amino-3-cyclohexyl(R)1-(2-thiazolyl)propan-1-ol.

15. A compound according to claim 1 N-[N-[(phenylmethoxy)carbonyl]-L-phenylalanyl-L-2-(ethoxy)-glycyl]-(S)2-amino-3-cyclohexyl(R)1-(2-pyridinyl)propan-1-ol.

16. A compound according to claim 3 N-[N-[(2-methylpropyl)carbonyl]-L-phenylalanyl-L-histidyl]-(S)2-amino-3-cyclohexyl-(R)1-(2-thienyl)propan-1-ol.

17. A compound according to claim 3 N-[N-[(2-methylpropyl)carbonyl]-L-phenylalanyl-L-2-1-methylethoxy)glycyl]-(S)2-amino-3-cyclohexyl-(R)1-(2-imidazolyl)propan-1-ol.

18. A compound according to claim 3 N-[N-[(2-methylpropyl)carbonyl]-L-phenylalanyl-L-2-(2-methylpropoxy)glycyl]-(S)2-amino-3-cyclohexyl-(R)1-(2-pyridinyl)propan-1-ol.

19. A compound according to claim 3 N-[N-[(2-methylpropyl)carbonyl]-L-tryptophyl-L-2-(2-methylethoxy)glycyl]-(S)2-amino-3-cyclohexyl-(R)1-(2-pyridinyl)propan-1-ol.

20. A compound according to claim 3 N-[N-[(2-methylpropyl)carbonyl]-L-3-(1-naphthyl)alanyl-L-2-(2-methypropyl)carbonyl -L-3-(1-naphthyl)alanyl-L-2-(2-methylpropoxy)glycyl]-(S)-2-amino-3-cyclohexyl-(R)1-(2-pyridinyl)propan-1-ol.

21. A compound according to claim 3 N-[N-[2-methylpropyl)carbonyl]-L-phenylalanyl-L-2-(2-N,N-dimethylaminoethylthio)glycly]-(S)-2-amino-3-cyclohexyl-(R)1-(2-thiazolyl)propan-1-ol.

22. A compound according to claim 3 N-[N-[(2-methylpropyl)carbonyl]-L-phenylalanyl-L-2-(2-N,N-dimethylaminoethoxy)glycyl]-(S)2-amino-3-cyclohexyl-(R)1-(2-pyridinyl)propan-1-ol.

23. A compound according to claim 3 N-[N-[(2-methylpropyl)carbonyl]-L-phenylalanyl-L-histidyl]-(S)2-amino-3-cyclohexyl-(R)1-(2-thienyl)propan-1-ol.

24. A compound according to claim 1 N-[N-[(1-naphthylmethoxy)carbonyl]-L-phenylalanyl L-2-(1-methylethoxy)glycyl]-(S)2-amino-3-cyclohexyl-(R)1-(2-pyrindinyl)propan-1-ol.

25. A compound according to claim 1 N-[N-[(phenylmethoxy)carbonyl]-L-phenylalanyl-L-2-(2-methylpropoxy)glycyl]-(S)2-amino-3-cyclohexyl-(R)-1-(2-thienyl)propan-1-ol.

26. A compound according to claim 1 N-[N-[(phenylmethoxy)carbonyl]-L-3-phenylalanyl-L-2-(1-methylethoxy)glycyl]-(S)2-amino-3-cyclohexyl-(R)1-(2-furanyl) propan-1-ol.

27. A compound according to claim 3 N-[N-(2-methylpropyl)carbonyl]-L-tryptophyl-L-histidyl]-(S)2-amino-3-cyclohexyl-(R)1-(2-thienyl)propan-1-ol.

28. A compound according to claim 8 N,N,-diethyl N-[N-[(2-methylpropyl)carbonyl]-L-phenylalanyl-L-2-(1-methylethoxy)glycyl]-5-[(S)2-amino-(R)1-hydroxy-3-cyclohexyl-propyl]2-thiopenecarboxamide.

29. A method of treating hypertension in a warm blooded animal which comprises administering to the animal a hypotensive amount of a compound of claim 1.

30. A parenteral composition in dosage unit form comprising a compound of claim 1 and a parenterally acceptable carrier.

* * * * *